US008377991B2

(12) United States Patent
van As

(10) Patent No.: US 8,377,991 B2
(45) Date of Patent: *Feb. 19, 2013

(54) TRANS-CLOMIPHENE FOR METABOLIC SYNDROME

(75) Inventor: Andre van As, West Chester, PA (US)

(73) Assignee: Repros Therapeutics Inc., The Woodlands, TX (US)

(*) Notice: Subject to any disclaimer, the term of this patent is extended or adjusted under 35 U.S.C. 154(b) by 14 days.

This patent is subject to a terminal disclaimer.

(21) Appl. No.: 13/196,688

(22) Filed: Aug. 2, 2011

(65) Prior Publication Data

US 2012/0022167 A1    Jan. 26, 2012

Related U.S. Application Data

(63) Continuation of application No. 12/205,456, filed on Sep. 5, 2008.

(60) Provisional application No. 60/980,334, filed on Oct. 16, 2007.

(51) Int. Cl.
*A61K 31/135* (2006.01)

(52) U.S. Cl. ...................................... 514/654

(58) Field of Classification Search ................ None
See application file for complete search history.

(56) References Cited

U.S. PATENT DOCUMENTS

| | | | |
|---|---|---|---|
| 4,061,733 A | 12/1977 | Gunjikar |
| 4,729,999 A | 3/1988 | Young |
| 4,820,736 A | 4/1989 | Jensen et al. |
| 4,894,373 A | 1/1990 | Young |
| 5,728,688 A | 3/1998 | Labrie |
| 5,861,389 A | 1/1999 | Radlmaier |
| 6,017,964 A | 1/2000 | MacLean et al. |
| 6,096,338 A | 8/2000 | Lacy |
| 6,126,969 A | 10/2000 | Shah |
| 6,129,933 A | 10/2000 | Oshlack |
| 6,143,353 A | 11/2000 | Oshlack |
| 6,190,591 B1 | 2/2001 | Van Lengerich |
| 6,221,399 B1 | 4/2001 | Rolfes |
| 6,248,363 B1 | 6/2001 | Patel |
| 6,291,505 B1 | 9/2001 | Huebner et al. |
| 6,342,250 B1 | 1/2002 | Masters |
| 6,391,920 B1 | 5/2002 | Fisch |
| 6,511,986 B2 | 1/2003 | Zhang et al. |
| 6,583,129 B1 | 6/2003 | Mazer et al. |
| 6,600,010 B2 | 7/2003 | Mao et al. |
| 6,638,528 B1 | 10/2003 | Kanios |
| 6,645,974 B2 | 11/2003 | Hutchinson et al. |
| 6,653,297 B1 | 11/2003 | Hodgen |
| 6,685,957 B1 | 2/2004 | Bezemer et al. |
| 6,743,448 B2 | 6/2004 | Kryger |
| 7,105,679 B2 | 9/2006 | Kanojia et al. |
| 7,354,581 B2 | 4/2008 | Cedarbaum et al. |
| 2002/0120012 A1 | 8/2002 | Fisch |
| 2002/0183296 A1 | 12/2002 | Dudley et al. |
| 2004/0097597 A1 | 5/2004 | Podolski et al. |
| 2004/0171697 A1 | 9/2004 | Podolski et al. |
| 2004/0220154 A1 | 11/2004 | Kryger |
| 2004/0241224 A1 | 12/2004 | Podolski et al. |
| 2006/0269611 A1 | 11/2006 | Steiner et al. |

FOREIGN PATENT DOCUMENTS

| | | |
|---|---|---|
| AU | 2001261684 | 12/2001 |
| EP | 0206021 A | 8/1988 |
| EP | 0430388 A2 | 6/1991 |
| EP | 0888775 A2 | 7/1999 |
| EP | 1090639 A3 | 11/2001 |
| EP | 1829534 A1 | 9/2007 |
| WO | WO 95/35093 | 12/1995 |
| WO | 00/05954 | 2/2000 |
| WO | WO 01/34117 A1 | 5/2001 |
| WO | WO 01/91744 A1 | 12/2001 |
| WO | 03/005954 A3 | 1/2003 |
| WO | WO 03/005954 A2 | 1/2003 |
| WO | WO 03/005954 A3 | 1/2003 |
| WO | WO 03/026568 A2 | 4/2003 |
| WO | WO 03/072092 | 9/2003 |
| WO | WO 2006-019916 A | 2/2006 |
| WO | WO 2006/084153 | 8/2006 |
| WO | WO 2006/102232 | 9/2006 |
| WO | WO 2007/019165 | 2/2007 |
| WO | WO 2009/051908 | 4/2009 |

OTHER PUBLICATIONS

U.S. Appl. No. 12/205,456 Restriction Requirement dated Apr. 30, 2010.
U.S. Appl. No. 12/205,456 Non-Final Office Action dated Sep. 28, 2010.
U.S. Appl. No. 12/205,456 Final Office Action dated Mar. 7, 2011.
U.S. Appl. No. 12/205,456 Non-Final Office Action dated Apr. 24, 2012.
Virginia Mason Medical Center (available online at www.virginiamason.org) accessed Mar. 2, 2011.
Williams, D., et al., Foye's Priciples of Medicinal Chemistry 5 Edition, Part I/Principles of Drug Discovery, Lippincott Williams & Wilkins, p. 50 (2002).
Clomid Information Sheet (available online at http//clomid.us) accessed Mar. 2, 2011.
ACCE Clinical Practice Guidelines for the Evaluation and Treatment of Hypogonadism in Adult Male Patients (1996).
Agarwal, et al., "Male Sexual Dysfunction After Stroke," J Assoc. Physicians India, vol. 37, No. 8, pp. 505-507 (1989).
Anonymous: "Zonagen Presents Data for Androxal in the Treatment of Hypogonadal Men and Data for Progenta as a Potential New Approach in the Treatment of Breast Cancer," News Release, The Healthcare Sales & Marketing Network, XP-002352050, Sep. 2, 2004.
Banner, A., et al., "Emerging Role of Corticosteroids in Chronic Obstructive Pulmonary Disease," The Lancet, vol. 354, pp. 440-441 (Aug. 7, 1999).
Barg, P., et al., "Male Factor: Clinical Evaluation of the Semen Analysis," Infert. Reprod. Med. Clin. North Amer., vol. 2, pp. 333-340 (1991).

(Continued)

*Primary Examiner* — Craig Ricci
(74) *Attorney, Agent, or Firm* — Morgan, Lewis & Bockius LLP

(57) ABSTRACT

The present invention relates to the administration of compositions comprising an antiestrogen, preferably trans-clomiphene, for treating metabolic syndrome in a subject. The invention is also directed to methods for reducing fasting glucose levels in a subject by administering a composition comprising an antiestrogen, preferably trans-clomiphene.

8 Claims, 10 Drawing Sheets

OTHER PUBLICATIONS

Bartsch, G., "The Effect of Antiestrogen, Antiandrogen, and the Prolactin Inhibitor 2 Bromo-'alpha!-ergocriptine on the Stromal Tissue of Human Benign Prostatic Hyperplasia. Correlation of Sterological Data and Plasma Hormones," Database Embase; Elsevier Science Publishers, Amsterdam, NL, 1981, vol. 18, No. 4, pp. 308-312.

Ben-Jonathan, N., et al., "Dopamine as a Prolactin (PRL) Inhibitor," Endocr. Rev. 22(6), pp. 724-763 (2001).

Bhasin, S., et al., "Testosterone Therapy in Adult Men with Androgen Deficiency Syndromes: An Endocrine Society Clinical Practice Guideline," J. Clin Endocrin, Metabol., vol. 91, pp. 1995-2010 (2006).

Breznik, R., et al., "Effectiveness of Antiestrogens in Infertile Men," Arch. Androl., vol. 31(1), pp. 43-48 (1993).

Brody, J., "Sperm Found Especially Vulnerable to Environment," The New York Times, Mar. 10, 1981.

Broulik, P.D., "Tamoxifen Prevents Bone Loss in Castrated Male Mice," Hormone and Metabolic Research, Thieme-Stratton, Stuttgart, DE, vol. 32, No. 5, pp. 181-184 (2000) XP009041862.

Burghardt, et al., "Gap Junction Modulation in Rat Uterus. III. Structure-Activity Relationships of Estrogen Receptor-Binding Ligands on Myometrial and Serosal Cells," Biol. Reprod. vol. 36, No. 3, pp. 741-751 (1977).

Casaburi, R., et al., "Effects of Testosterone and Resistance Training in Men with Chronic Obstructive Pulmonary Disease," American Journal of Respiratory and Critical Care Medicine, vol. 170, pp. 870-878 (2004).

Chakraborty, P. et al., "Effects of Long-Term Treatment With Estradiol or Clomiphene Citrate on Bone Maintenance, and Pituitary and Uterine Weights in Ovariectomized Rats," J. Steroid Biochem. Molec. Biol., vol. 40, No. 4-6, pp. 725-729 (1991).

Chang, Ching-Fong, et al., "Stimulation of Ovulation in Ayu Plecoglossus-altivelis by Treatment with Antiestrogens and Luteinizing Hormone-Releasing Hormone Analog," Aquaculture, vol. 101, Nos. 3-4, pp. 329-336 (1992).

Check, J., et al., "Empirical Therapy of the Male with Clomiphene in Couples with Unexplained Infertility" Int. Journal Fertil., vol. 34(2), pp. 120-122 (1989).

Cooper, A., et al., "The Effects of Clomiphene in Impotence A Clinical and Endocrine Study," British Journal of Psychiatry, vol. 120, pp. 327-330 (1972).

Cunningham, G., et al., "Testosterone Replacement Therapy and Sleep-Related Erections in Hypogonadal Men," J. Clin. Endocrinol. Metab., vol. 70, No. 3, pp. 792-797 (1990).

Dangprasit, P., et al., "Development of Diclofenac Sodium Controlled Release Solid Dispersions by Spray Drying Using Optimization Strategy I. Powder Formulation," Drug. Devel. and Industrial Pharm. 21(20), pp. 2323-2337 (1995).

Davidson, J., et al., "Effects of Androgen on Sexual Behavior in Hypogonadal Men," J. Clin. Endocrinol. Metab., vol. 48, No. 6, pp. 955-958 (1979).

Debigare, R., et al., "Peripheral Muscle Wasting in Chronic Obstructive Pulmonary Disease," American Journal of Respiratory and Critical Care Medicine, vol. 164, pp. 1712-1717 (2001).

Drew, A., "Letter: Possibe Teratogenic Effect of Clomifene," Developmental Medicine and Child Neurology, vol. 16, No. 2, pp. 276 (1974).

Eil, "Ketoconazole Binds to the Human Androgen Receptor," Horm Metab Res., vol. 24, No. 8, pp. 367-370 (1992).

Elanjian, Sona I., "Clomiphene for Male Infertility," Journal of Pharmacy Technology, vol. 12, No. 3, pp. 102-104 (1996).

EP Supplementary Search Report of EP 02748104 dated Jun. 24, 2005.

EP Supplementary Search Report of EP 06720243 dated Aug. 6, 2008.

EP Supplementary Search Report of EP 06738985 dated Aug. 15, 2008.

EP Supplementary Search Report of EP 06800648 dated Jul. 21, 2008.

Epstein, "Clomiphene Treatment in Oligospermic Infertile Males," Fertility and Sterility, vol. 28, No. 7, pp. 741-745 (1977).

Ernst, S., et al., "Stereochemistry of Geometric Isomers of Clomiphene: A Correction of the Literature and a Reexamination of Structure-Activity Relationships," J. Pharmaceut. Sci., vol. 65, No. 1, pp. 148-150 (1976).

Excerpt on www.medscape.com from Drug Ther. Perspect., vol. 10, pp. 1-5 (1997).

Feldman, H., et al., "Age Trends in the Level of Serum Testosterone and Other Hormones in Middle-Aged Men: Longitudinal Results form the Massachusetts Male Aging Study," J Clin Endocrinol Metab. 87(2), pp. 589-598 (2002).

Fitzpatrick, S., et al., "Effect of Estrogen Agonists and Antagonists on Induction of Progesterone Receptor in a Rat Hypothalamic Cell Line," Endocrinology, vol. 140, No. 9, pp. 3928-3937 (1999).

Fuse, H., et al., "Changes in Seminal Plasma Transferring Concentration Following Administration of Clomiphene Citrate," Archives of Andrology, vol. 31, pp. 139-145 (1993).

Garg, Abhimanyu, "Medical progress: Acquired and Inherited Lipodystrophies," New England Journal of Medicine, vol. 35, No. 12, pp. 1231-1232 (2004).

Glasier, A., et al., "A Comparison of the Effects on Follicular Development Between Clomiphene Citrate its Two Separate Isomers and Spontaneous Cycles," Human Reproduction, vol. 4, No. 3, pp. 252-256 (1989).

Grinenko, et al., Khimiko-farmatsevticheskii Zhurnal, vol. 23, No. 1, pp. 123-126 (1989).

Guay A., et al., "Results of Double Blinded Treatment With Clomiphene Citrate in Patients With Hypogoadotropic Hypogonadism," Annual Meeting of the Endocrine Society, Abstract No. 386, (Jun. 1993).

Guay, A., et al., "Effect of Raising Endogenous Testosterone Levels in Impotent Men with Secondary Hypogonadism: Double Blind Placebo-Controlled Trial with Clomiphene Citrate," Journal of Clinical Endocrinology and Metabolism, vol. 80, No. 12, pp. 3546-3552 (1995).

Guay, A., et al., "Possible Hypothalamic Impotence," Urology, vol. 38, No. 4, pp. 317-322 (1991).

Guay, A., et al., "Clomiphene Increases Free Testosterone Levels in Men with Both Secondary Hypogonadism and Erectile Dysfunction: Who Does and Does Not Benefit?" Internatl. J. Ompot. Res., vol. 15, pp. 156-165 (2003).

Guzick, D., et al., "Sperm Morphology, Motility and Concentration in Fertile and Infertile Men," N. Engl. J. Med., vol. 345, pp. 1388-1393 (2001).

Hanus, M., et al., "Antiestrogens (Tamoxifen) in the Alternative Therapy of Benign Prostatic Hyperplasial," US National Library of Medicine, Bethesda, MD, Databse Medline, vol. 72, No. 7, pp. 316-318 (1993).

Haskell, S., "Selective Estrogen Receptor Modulators," Southern Medical Journal, vol. 96, No. 5, pp. 469-476 (2003).

Hayashi, Norio, et al., Hinyokika Kiyo (Acta Urologica Japonica), vol. 34, No. 5, pp. 847-850 (1988) with English translation.

Herzog, A. G., "Reproductive Endocrine Considerations and Hormonal Therapy for Men with Epilepsy," Epilepsia, Raven Press Ltd., New York, US (1991), vol. 32, No. Suppl. 6, pp. S34-S37.

Hirshkowitz, M., et al., "Androgen and Sleep-Related Erections," J. Psychosomatic Research, vol. 42, No. 6, pp. 541-546 (1997).

Homonnai, Z., et al., "Clomiphene Citrate Treatment in Oligozoospermia: Comparison Between Two Regimens of Low-Dose Treatment," Fertility and Sterility., vol. 60, No. 5, pp. 801-804 (1988).

International Preliminary Examination Report of PCT/US02/21524 dated Mar. 3, 2006.

International Preliminary Report on Patentability of PCT/US05/02500 dated Jan. 16, 2007.

International Preliminary Report on Patentability of PCT/US06/003882 dated Aug. 7, 2007.

International Preliminary Report on Patentability of PCT/US06/030053 dated Feb. 5, 2008.

International Preliminary Report on Patentability of PCT/US06/10022 dated Sep. 25, 2007.

International Search Report of PCT/US02/21524 dated Jun. 18, 2003.

International Search Report of PCT/US05/02500 dated Nov. 24, 2005.

International Search Report of PCT/US06/003882 dated Aug. 14, 2006.
International Search Report of PCT/US06/10022 dated Jan. 10, 2007.
International Search Report of PCT/US06/30053 dated Dec. 22, 2006.
International Search Report of PCT/US09/063621 dated Dec. 28, 2009.
Jarow, J., "Nonsurgical Treatment of Male Infertility: Empiric Therapy," Therapy, Chapter 23, pp. 410-422 (1991).
Jiann, B., et al., "Effect of Clomiphene on $Ca^{2+}$ Movement in Human Prostate Cancer Cells," Life Sciences, vol. 70, No. 26, pp. 3167-3178 (May 2002).
Jimenez, M., et al., "Clomiphene Prevents Cancellous Bone Loss from Tibia of Ovariectomized Rats," vol. 138, No. 5, pp. 1794-1800 (1997).
Kadioglu, et al., Treatment of Idiopathic and Postvaricocelectomy Oligozoospermia with Oral Tamoxifen Citrate, BJU Int., vol. 83, No. 6, pp. 646-648 (1999).
Ke, H. Zhu, et al., "Lasofoxifene (CP-336,156), A Selective Estrogen Receptor Modulator, Prevents Bone Loss Induced by Aging and Orchidectomy in the Adult Rat," Endocrinology, vol. 141, No. 4, pp. 1338-1344 (2000) XP001170303.
Kharenko, A., et al., "Controlled Release From Oral Formulations Based on Interpolymeric Polymethacrylic Acid-Polyethylene Glycol Complex," Proceed. Intern. Symp. Control Rel. Bioact. Mater., vol. 22, pp. 232-233 (1995).
Kidd, S., et al., "Effects of male age on semen quality and fertility: A review of the literature," Fertility and Sterility, vol. 75, pp. 237-248 (2001).
Kotoulas, et al., "Tamoxifen Treatment in Male Infertility. I. Effect on spermatozoa," Fertil. Steril., vol. 61, No. 5, pp. 911-914 (1994).
Laghi, F., et al., "Respiratory and Skeletal Muscles in Hypogonadal Men with Chronic Obstructive Pulmonary Disease," American Journal of Respiratory and Critical Care Medicine, vol. 171, pp. 598-605 (2005).
Lewis, B., et al., "Medical Implication of the Biological Clock," JAMA, vol. 296, pp. 2369-2371 (2006).
Lim, V., et al., "Restoration of Plasma Testosterone Levels in Uremic Men with Clomiphene Citrate," Journal of Clinical Endocrinology and Metabolism, New York, US vol. 43, No. 6, pp. 1370-1377 (1976) XP 009041861.
Lund, et al., "Testosterone and Andropause: The Feasibility of Testosterone Replacement Therapy in Elderly Men," Pharmacotherapy, vol. 19, No. 8, pp. 951-956 (1999).
Macleod, J., et al., "The Male Factor in Fertility and Infertility II Spermatozoon Counts in 1000 Men of Known Fertility and in 1000 Cases of Infertile Marriage," J. Urology, vol. 66, pp. 436-449 (1951).
Matsumoto, A., et al., "Human Chorionic Gonadotropin and Testicular Function: Stimulation of Testosterone, Testosterone Precursors, and Sperm Production Despite High Estradiol Levels," Journal of Clinical Endocrinol. and Metab., vol. 56, No. 4, pp. 720-728 (1983).
McKinlay, et al., "The Questionable Physiologic and Epidemiologic Basis for a Male Climacteric Syndrome: Preliminary Results from the Massachusetts Male Aging Study," Maturitas, vol. 11, No. 2, pp. 103-115 (1989).
Medical Information of Henan Province, "Report on 42 Cases of Treating Male Sterility with Clomiphene," vol. 2, No. 2 (Feb. 2001) (Translation).
Merck Index, 13th Ed., Entry 2410, p. 417 (2001).
Meshali, M., et al., "Effect of Interpolymer Complex Formation of Chitosan With Pectin or Acaxia on the Release Behaviour of Chlorpromazine HCl" Int. J. Phar., vol. 89, pp. 177-181 (1993).
Morales, A., et al., "Andropause: A Misnomer for a True Clinical Entity," J. Urol., vol. 163, No. 3, pp. 705-712 (2000) Abstract.
Parini, et al., "Importance of Estrogen Receptors in Hepatic LDL Receptor Regulation," Ateriosclerosis, Thrombosis, and Vascular Biology, vol. 17, pp. 1800-1805 (1997).
PCT Written Opinion of PCT/US02/21524 dated Nov. 25, 2005.
PCT Written Opinion of PCT/US05/02500 dated Sep. 14, 2006.
PCT Written Opinion of PCT/US06/003882 dated Aug. 4, 2007.
PCT Written Opinion of PCT/US06/10022 dated Jan. 10, 2007.
PCT Written Opinion of PCT/US06/30053 dated Dec. 22, 2006.
PCT Written Opinion of PCT/US08/075433 dated Dec. 19, 2008.
PCT Written Opinion of PCT/US09/063621 dated Dec. 28, 2009.
Petak, S., et al., American Association of Clinical Endocrinologists Medical Guidelines for Clinical Practice for the Evaulation and Treatment of Hypogonadism in Adult Male Patients, Endocrine Practice, vol. 8, pp. 439-456 (2002).
Purvis, K., et al., "Stability of Sperm Characteristics in Men with Disturbances in Sperm Quality," Int. Journal Androl., 12, pp. 171-178 (1989).
Ronnberg, "The Effect of Clomiphene Treatment on Different Sperm Parameters in Men with Idiopathic Oligozoospermia," Andrologia, vol. 12, No. 1, pp. 261-265 (1980).
Schultheiss, D., et al., "Testosterone Therapy in the Ageing Male: What About the Prostate?" Andrologia, vol. 36, No. 6, pp. 357-365 (2004).
Schweikert, et al., "Effects of Estrogen Deprivation on Human Benign Prostatic Hyperplasia," Steroid Biochem Mol Biol., vol. 44, No. 4-6, pp. 573-576 (1993).
Shanis, et al., Adverse Effect of Clomiphene Citrate on Sperm Morphology, Arch. Androl., vol. 21, pp. 109 (1991).
Shida, K., et al., "Medical Treatment of Neoplasm with Steroids and Antisteroids," Chemical Abstracts Service, XP-002352053, May 12, 1984.
Shirai, Takashi, et al., Saishin-Igaku (Latest Medical Science), vol. 45, No. 11, pp. 2250-2254 (1990) with English translation.
Singh, S., et al., "Changes in Fructose & Citric Acid in Accessory Glands of Reproduction of Rats Following Long-Term Treatment With Isomers of Clomiphene Citrate," Indian Journal of Experimental Biology, vol. 11, pp. 23-26 (Jan. 1973).
Soderguard, R., et al., "Calculation of Free and Bound Fractions of Testosterone and Estradiol-17β to Human Plasma Proteins at Body Temperature," J. Steroid Biochem, vol. 16, pp. 801-810 (1982).
Sokol, "A Controlled Comparison of the Efficacy of Clomiphene Citrate in Male Infertility," No. 5, Fertil and Steril, vol. 49, pp. 865-870 (1988).
Stahl, F., et al., "Effects of Tamoxifen on the Levels of luteinizing Hormone (LH), Follicle Stimulating Hormone FSH), Prolactin (PRL), 17 beta-oestradiol (E2), and free dihydrotestosterone (DHT) in blood of patients with Benign Prostatic Hyperplasia," US National Library of Medicine, Bethesda, MD, US, vol. 82, No. 1, pp. 21-28 (1983).
Stedman's Medical Dictionary, William and Wilking, pp. 1312, 1439 & 1798-1799 (1995).
Steiner, et al., "Antiestrogens and Selective Estrogen Receptor Modulators Reduce Prostte Cancer Risk," World J Urol., vol. 21, pp. 31-36 (2003).
Sternbach, et al., "Age-associated Testosterone Decline in Men: Clinical Issues for Psychiatry," Am. J. Psychiatry, vol. 155, No. 10, pp. 1310-1318 (1998) Abstract.
Sterochemistry of Geometric Isomers of Clomiphene: A Correction of the Literature and a Reexamination of Structure-Activity Relationships, Journal of Pharmaceutical Science, vol. 65, No., pp. 184-150 (176) XP009056304.
Suzuki, et al., "Endocrine Environment of Benign Prostatic Hyperplasia: Prostate Size and Volume are Correlated with Serum Estrogen Concentration," Scand. J. Urol. Nephrol., vol. 29, No. 1, pp. 65-68 (1995) Abstract.
Takihara, Hiroshi, Jin to Toseki (Kidney and Dialysis) vol. 41, Special Edition, pp. 759-761 (1996) with English translation.
Tenover, J., et al., J Clin. Endocrine. Metabol., vol. 75, pp. 1092-1098 (1992).
Tenover, J., et al., "Male Hormone Replacement Therapy Including Andropause," Endocrinology and Metabolism Clinics of North America, W.B. Saunders Company, Philadelphia, US, Dec. 1998, vol. 27, No. 4, pp. 969-987 XP008019800.
Tenover, J., et al., "Serum Bioactive and Immunoreactive Follicle-Stimulating Hormone Levels and the Response to Clomiphene in Healthy Young and Elderly Men," Journal Clinical Endocrinol. and Metab., vol. 64, No. 6, pp. 1103-1108 (1987).
Tenover, J., et al., "The Effects of Aging in Normal Men on Bioavailable Testosterone and Luteinizing Hormone Secretion: Response to Clomiphene Citrate," Journal Clinical Endocrinol. Metab. , vol. 65, No. 6, pp. 1118-1126 (1987).

Turner, R., et al., "Differential Responses of Estrogen Target Tissues in Rats Including Bone to Clomiphene, Enclomiphene, and Zuclomiphene," vol. 139, No. 9, pp. 3712-3720 (1998).

U.S. Pharmacopeia, United States Phamacopeia, 26th Ed., pp. 484-485 (2003).

Vippagunta, et al., Advanced Drug Delivery Reviews, vol. 48, pp. 3-26 (2001).

Weissenberg, R., et al., "The Effect of Clomiphene Citrate and is Zu or En isomers on the Reproductive System of the Immature Male Rate," Andrologia, vol. 24, pp. 161-165 (1992).

Wiehle, R.D., et al., "Androxal™ (oral enclomiphene citrate) Raises Free and Total Serum Testosterone in Hypogonadal Men: Comparison with Androgel 1%®," Fertility and Sterility, vol. 82, pp. 2004-2009, (2004).

Written Opinion of Singapore Patent Applc. 2007-05640-1 dated Jul. 9, 2008.

Young, R., et al., "A Short-Term Comparison of the Effects of Clomiphene Citrate and Conjugated Equine Estrogen in Menopausal/Castrate Women," Int. J. Fertil., vol. 36, No. 3, pp. 167-171 (1991).

Young, R., et al., "Qualitative Differences in Estrogenic/Antiestrogenic Effects of Clomiphene and Zuclomiphene," Int. J. Fertil., vol. 36, No. 5, pp. 291-295 (1991).

U.S. Appl. No. 10/427,768 Examiner's Interview Summary Record dated Nov. 19, 2007.

U.S. Appl. No. 10/427,768 Final office action dated Apr. 6, 2006.

U.S. Appl. No. 10/427,768 Non-final office action dated May 29, 2007.

U.S. Appl. No. 10/427,768 Non-final office action dated Oct. 12, 2005.

U.S. Appl. No. 10/427,768 Notice of Allowance and Examiner's Amendment dated Dec. 27, 2007.

U.S. Appl. No. 10/427,768 Restriction Requirement dated May 23, 2005.

U.S. Appl. No. 10/483,458 Non-final office action dated Jul. 20, 2009.

U.S. Appl. No. 10/483,458 Advisory Action dated Jan. 16, 2009.

U.S. Appl. No. 10/483,458 Final office action dated Nov. 19, 2008.

U.S. Appl. No. 10/483,458 Non-final office action dated Feb. 13, 2008.

U.S. Appl. No. 10/483,458 Restriction Requirement dated Oct. 25, 2007.

U.S. Appl. No. 10/712,546 Non-final office action dated Mar. 15, 2006.

U.S. Appl. No. 10/712,546 Notice of Allowance dated Sep. 29, 2006.

U.S. Appl. No. 10/712,546 Restriction Requirement dated Nov. 10, 2005.

U.S. Appl. No. 11/750,190 Restriction Requirement dated Mar. 27, 2009.

U.S. Appl. No. 11/750,190 Non-final office action dated Aug. 11, 2009.

U.S. Appl. No. 11/750,190 Notice of Allowance dated Jan. 8, 2010.

U.S. Appl. No. 11/571,150 Restriction Requirement dated Aug. 31, 2009.

U.S. Appl. No. 11/571,150 Non-final office action dated Oct. 14, 2009.

U.S. Appl. No. 11/997,858 Restriction Requirement dated Aug. 28, 2009.

U.S. Appl. No. 11/815,542 Restriction Requirement dated Aug. 31, 2009.

U.S. Appl. No. 11/815,542 Non-final office action dated Oct. 15, 2009.

U.S. Control No. 90/008,024 Non-final office action dated Nov. 1, 2006.

U.S. Control No. 90/008,024 Examiner Interview Summary Record dated Dec. 13, 2006.

U.S. Control No. 90/008,024 Non-final office action dated Jan. 29, 2007.

U.S. Control No. 90/008,024 Final office action dated Jun. 22, 2007.

U.S. Control No. 90/008,024 Examiner Interview Summary Record dated Jul. 25, 2007.

U.S. Control No. 90/008,024 Final office action dated Nov. 16, 2007.

U.S. Control No. 90/008,024 Advisory Action dated Feb. 1, 2008.

U.S. Control No. 90/008,024 Advisory Action dated Mar. 5, 2008.

U.S. Control No. 90/008,024 Examiner's Answer dated Jun. 12, 2008.

U.S. Control No. 90/006,921 Non-final office action dated Sep. 9, 2004.

U.S. Control No. 90/006,921 Examiner's Interview Summary dated Oct. 20, 2004.

U.S. Control No. 90/006,921 Final office action dated Feb. 23, 2005.

U.S. Control No. 90/006,921 Petition Decision dated May 25, 2005.

U.S. Control No. 90/006,921 Non-final office action dated Jun. 27, 2005.

International Search Report of PCT/US2008/075433 dated Dec. 19, 2008.

Jones, T. Hugh., "Testosterone Associations with Erectile Dysfunction, Diabetes, and the Metabolic Syndrome," European Urology Supplements, vol. 6, pp. 847-857 (2007).

U.S. Appl. No. 12/838,036 Non-Final Office Action dated Oct. 21, 2010.

U.S. Appl. No. 12/838,036 Final Office dated May 16, 2011.

U.S. Appl. No. 10/483,458 Final Office dated Mar. 17, 2010.

U.S. Appl. No. 10/483,458 Notice of Allowance dated Apr. 21, 2010.

U.S. Appl. No. 11/750,190 Notice of Allowance dated Feb. 5, 2010.

U.S. Appl. No. 11/815,542 Non-final office action dated May 10, 2011.

U.S. Appl. No. 11/815,542 Final Office action dated Nov. 15, 2011.

U.S. Appl. No. 11/815,542 Non-Final Office Action dated Feb. 28, 2012.

U.S. Appl. No. 11/815,542 Notice of Allowance dated Apr. 18, 2012.

U.S. Appl. No. 11/814,068 Non-final office action dated Apr. 12, 2011.

U.S. Control No. 90/008,024 Decision on Appeal dated Aug. 28, 2009.

U.S. Control No. 90/008,024 Decision on Request for Rehearing dated Aug. 2, 2010.

EP Extended Search Report for EP 11153365.9 dated Jan. 20, 2012.

Anonymous: Ferring Arzneimittel: "Clomifen Ferring 50 mg Tabletten," (http://ww.fachinfo.de/data/fi/jsearch?wirkstoff retrieved on May 31, 2011) pp. 1-5 (XP007918978) Oct. 1, 2010.

Healthline, Hypogonadotropic Hypogonadism, reviewed by Robert Cooper, MD, accessed Oct. 15, 2010 pp. 1-2.

Makhsida, N., et al., "Hypogonadism and Metabolic Syndrome: Implications for Testosterone Therapy," J. Urology, vol. 174, pp. 827-834 (2005).

Macrochem Press Release (Opterone Topical Testosterone Cream, accessed online Sep. 20, 2010).

Mikkelson, T., et al., "Single-Dose Pharmacokinetics of Clomiphene Citrate in Normal Volunteers," Fertility and Sterility, vol. 46, No. 3, pp. 392-396 (1986).

Ross., J.W., et al., "Effect of Clomiphene Citrate and Its Isomers on Sexual Behavior in Ovariectomized Rats," Endocrinology, vol. 92, No. 4, pp. 1079-1083 (Apr. 1973) (Abstract).

Young S., "Serum Concentrations of Enclomiphene and Zuclomiphene Across Consecutive Cycles of Clomiphene Citrate Therapy in Anovulatory Infertile Women," Fertility anda Sterility, vol. 71, No. 4, pp. 639-644 (1999).

TRANS-CLOMIPHENE FOR METABOLIC SYNDROME

CROSS-REFERENCE TO RELATED APPLICATIONS

This application is a continuation of U.S. application Ser. No. 12/205,456, filed Sep. 5, 2008, which claims the benefit of U.S. Provisional Application Ser. No. 60/980,334, filed Oct. 16, 2007, the contents of which is are hereby incorporated by reference.

FIELD OF THE INVENTION

The present invention relates to compositions and methods for treating metabolic syndrome and conditions associated therewith. More specifically, the present invention relates to the use of compositions comprising clomiphene enriched for trans-clomiphene for treating metabolic syndrome and conditions associated therewith in subjects with low or low normal testosterone.

BACKGROUND

Metabolic syndrome is characterized by a group of metabolic risk factors in one person including abdominal obesity, insulin resistance or glucose intolerance, atherogenic dyslipidemia, prothrombotic state, proinflammatory state and hypertension. The Adult Treatment Panel defines metabolic syndrome as present if a patient manifests at least three of the following symptoms: waist measuring at least 40 inches for men, 35 inches for women; serum triglyceride levels of at least 150 mg/dl; HDL cholesterol levels of less than 40 mg/dl in men, less than 50 mg/dl in women, blood pressure of at least 135/80 mm Hg and blood sugar (serum glucose) of at least 110 mg/dl. It has been estimated that up to 25% of the population in the United States are afflicted with metabolic syndrome.

An underlying cause of metabolic syndrome is believed to be insulin resistance wherein the ability of insulin to take in glucose from the blood is attenuated. This causes glucose levels to remain elevated after eating to which the pancreas responds by excreting insulin. If left untreated, metabolic syndrome significantly increases the risk of type II diabetes, cardiovascular disease and other diseases related to plaque buildups in artery walls.

An inverse correlation between fasting insulin levels and serum testosterone in men has been demonstrated by several studies. Moreover, serum testosterone is significantly lower in men with metabolic syndrome and other insulin-resistant states such as obesity and type 2 diabetes mellitus compared to controls. The mechanism underlying these observations, however, has not been elucidated.

One recent study has suggested that the relationship between testosterone and insulin may be mediated through changes in the body mass index (BMI) wherein low testosterone levels lead to obesity and dysregulation of fatty acid metabolism which in turn promotes insulin resistance. In contrast to testosterone, no significant relationship between estrogen levels and insulin sensitivity was found in that study.

Another recent study evaluated the hypothalamic-pituitary-gonadal axis in men with a broad spectrum of insulin sensitivity. In this study, a positive relationship between insulin sensitivity and testosterone was observed, however, no relationship was observed between insulin sensitivity and luteinizing hormone (LH) secretion parameters suggesting that low testosterone associated with insulin resistance does not result from a defect in the hypothalamus or pituitary, but rather from an alteration in Leydig cell function. In this regard, it well established that Leydig cell steroidogenesis, at least in vitro, is modulated not only by pulsatile secretion of LH but also by hormones, growth factors, cytokines and insulin.

Data on the impact of androgen supplementation on insulin sensitivity in men are conflicting. In one study, men with type 2 diabetes showed no improvement in glycemic control with testosterone replacement, whereas a larger study showed a significant reduction in glycosylated hemoglobin.

Testosterone is the primary male androgen, playing a vital role in overall male health. Testosterone is essential to the development and maintenance of specific reproductive tissues (testes, prostate, epididymis, seminal vesicle, and penis) and male secondary sex characteristics. It plays a key role in libido and erectile function and is necessary for the initiation and maintenance of spermatogenesis.

Testosterone secretion is the end product of a series of hormonal processes. Gonadotropin-releasing hormone (GnRH), which is secreted in the hypothalamus, controls the pulsatile secretion of luteinizing hormone (LH) and follicle stimulating hormone (FSH), which is secreted by the anterior pituitary. LH, in turn, regulates the production and secretion of testosterone in the Leydig cells of the testes, while FSH assists in inducing spermatogenesis.

Testosterone deficiency can result from underlying disease or genetic disorders and is also frequently a complication of aging. For example, primary hypogonadism results from primary testicular failure. In this situation, testosterone levels are low and levels of pituitary gonadotropins (LH and FSH) are elevated. Secondary or hypogonadotrophic hypogonadism is due to inadequate secretion of the pituitary gonadotropins. In addition to a low testosterone level, LH and FSH levels are low or low-normal. Some of the sequelae of adult testosterone deficiency include a wide variety of symptoms including: loss of libido, erectile dysfunction, oligospermia or azoospermia, absence or regression of secondary sexual characteristics, progressive decrease in muscle mass, fatigue, depressed mood and increased risk of osteoporosis. Many of these disorders are generically referred to as male menopause.

Clomiphene (FIG. 2), which is an antiestrogen related to tamoxifen, has also been used to treat men with low testosterone levels. Clomiphene blocks the normal estrogen feedback on the hypothalamus and subsequent negative feedback on the pituitary. This leads to increases in luteinizing hormone (LH) and follicle stimulating hormone (FSH). In men, these increased levels of gonadotropins stimulate the Leydig cells of the testes and result in the production of higher testosterone levels.

Tenover et al., J. Clin. Endocrinol. Metab. 64:1103, (1987) and Tenover et al., J. Clin. Endocrinol. Metab. 64:1118 (1987) found increased in FSH, LH in both young and old men after treatment with clomiphene. They also found increases in free and total testosterone in men with young men showing significant increases.

Ernst et al., J. Pharmaceut. Sci. 65:148 (1976), have shown that clomiphene is a mixture of two geometric isomers which they refer to as cis, -Z- , clomiphene (cis-clomiphene or zuclomiphene) and trans-, E-, clomiphene, (trans-clomiphene or enclomiphene). According to Ernst, et al. trans-clomiphene HCl has a melting point of 149° C.-150.5° C., while cis-clomiphene HCl has a melting point of 156.5° C.-158° C. Ernst et al. have also noted that (the trans-isomer) is antiestrogenic (AE) while the cis-isomer is the more potent and more estrogenic form and has also been reported to have anti-estrogenic activity. The authors attribute the effect of the drug on ovulatory activity to both forms stating that the mixture is more effective than trans-clomiphene alone. The trans-isomer aids ovulation at the level of the hypothalamus. The estrogenic isomer cis-clomiphene contributes to enhanced ovulation elsewhere in the physiologic pathway leading to ovulation. The isomers are also reported to have different in vivo half-life. Furthermore the cis form has been reported to leave residual blood levels for in excess of one month following a single dose.

Clomiphene is currently approved as a mixture of both cis- and trans-isomers, the cis-isomer being present as about 30% to 50% (Merck Manual) for fertility enhancement in the anovulatory patient. Clomiphene improves ovulation by initiating a series of endocrine events culminating in a preovulatory gonadotropin surge and subsequent follicular rupture. The drug is recommended to be administered for 5 days at a dose of up to 100 mg daily. Clomiphene has also been associated with numerous side effects including: blurred vision, abdominal discomfort, gynecomastia, testicular tumors, vasomotor flushes, nausea, and headaches. Furthermore, other studies suggest that clomiphene possesses both genotoxic and tumor enhancement effects. The net outcome of these observations is that clomiphene in its current format, having between 30% and 50% of the cis isomer, would be unacceptable for chronic therapy in men for the treatment of testosterone deficiency.

SUMMARY

The present invention is related to a method of treating metabolic syndrome comprising administering to a subject in need thereof, a composition comprising an effective amount of an antiestrogen or a pharmaceutically acceptable salt thereof. The subject may be male or female. The subject may also have idiopathic or secondary hypogonadotrophic hypogonadism.

The present invention is also related to a method of treating metabolic syndrome in a subject comprising administering to a subject in need thereof, an effective amount of a composition comprising 0% to 29% weight/weight of (cis, -Z-, trans-clomiphene) (hereinafter "cis-clomiphene") and 100% to 71% w/w (trans-, E-, cis-clomiphene) (hereinafter "trans-clomiphene") or a pharmaceutically acceptable salt thereof. The composition may consist essentially of trans-clomiphene or a salt thereof. The composition may also consist of trans-clomiphene or an analog thereof. The subject may be male or female. The subject may also have idiopathic or secondary hypogonadotrophic hypogonadism.

The present invention is also related to a method of treating one or more symptoms of metabolic syndrome comprising administering to a subject in need thereof, a composition comprising an effective amount of an antiestrogen or a pharmaceutically acceptable salt thereof. The subject may be male or female. The subject may also have idiopathic or secondary hypogonadotrophic hypogonadism.

The present invention is also related to a method for treating impaired fasting glucose in a subject comprising administering to a subject a composition comprising an effective amount of an antiestrogen or a pharmaceutically acceptable salt thereof. The subject may be male or female. The subject may be a male or female with a desire or need to reduce fasting glucose levels. The subject may also have idiopathic or secondary hypogonadotrophic hypogonadism.

The present invention is also related to a method for treating impaired fasting glucose in a subject comprising administering to a subject a composition comprising 0% to 29% weight/weight of (cis, -Z-, trans-clomiphene) (hereinafter "cis-clomiphene") and 100% to 71% w/w (trans-, E-, cis-clomiphene) (hereinafter "trans-clomiphene") or a pharmaceutically acceptable salt thereof. The composition may consist essentially of trans-clomiphene or a salt thereof. The composition may also consist of trans-clomiphene or an analog thereof. The subject may be a male or female with a desire or need to reduce serum glucose levels. The subject may also have idiopathic or secondary hypogonadotrophic hypogonadism.

DETAILED DESCRIPTION

Figure 1:
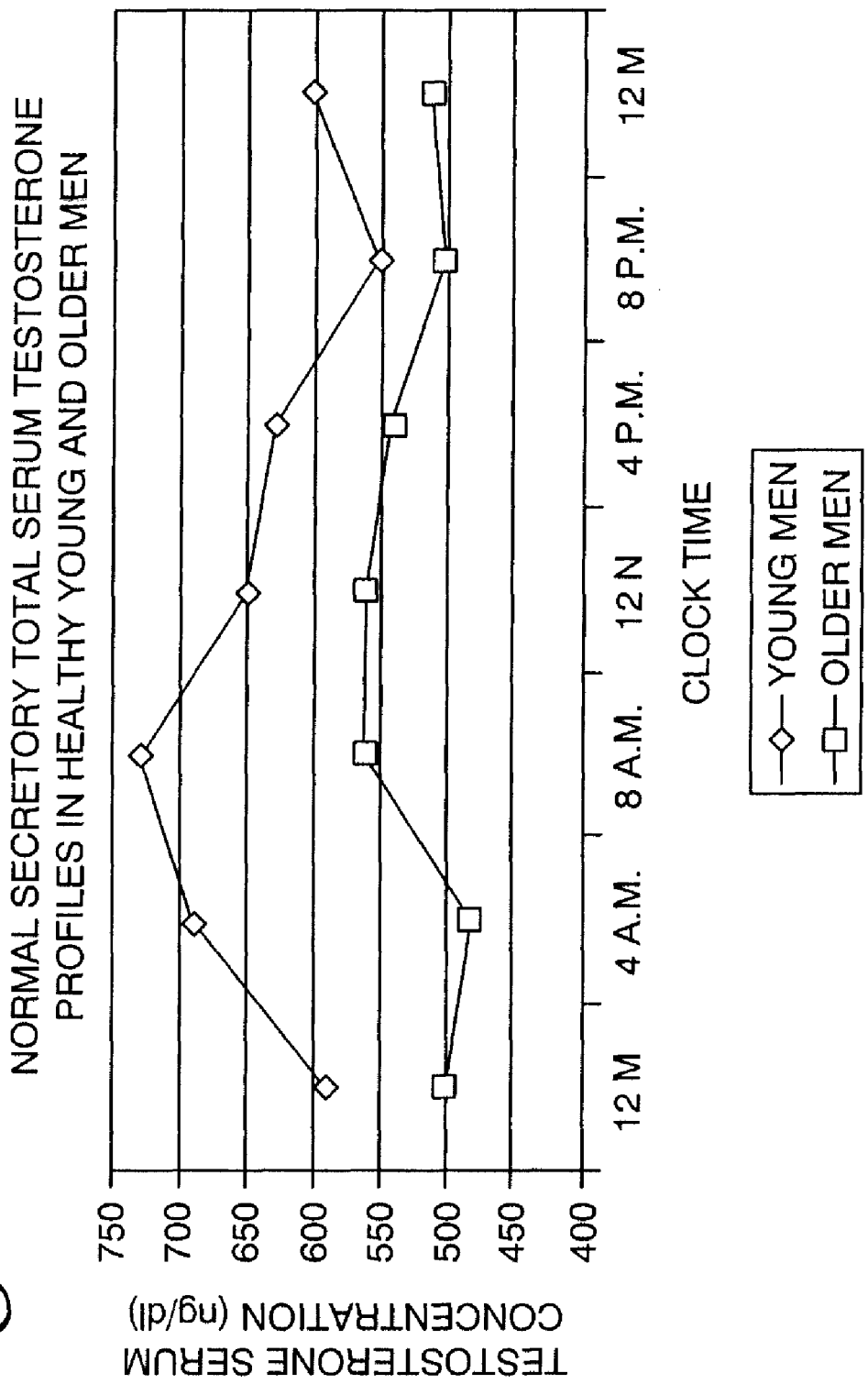
FIG. 1 is a graphic representative of the normal secretory total serum testosterone profiles in healthy men (young and old).
Figure 2:
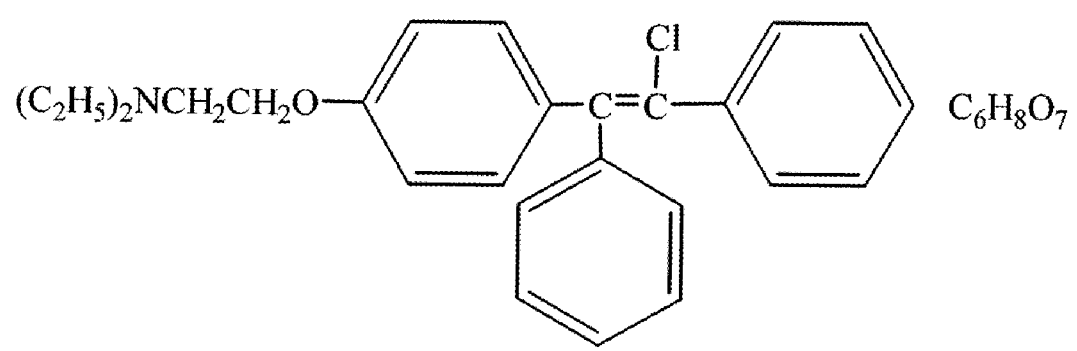
FIG. 2 shows the chemical structure of clomiphene citrate.

The present invention provides methods for treating metabolic syndrome and conditions associated therewith. The present invention is based on the surprising discovery that administration of a composition comprising trans-clomiphene to subjects with low total testosterone causes a decrease in fasting serum glucose levels concomitant with an increase in testosterone levels and a decrease in cholesterol and triglyceride levels in the subjects. Thus, compositions comprising trans-clomiphene are surprisingly useful in treating metabolic syndrome. The discovery is unexpected in view of recent studies suggesting: (1) that insulin resistance associated with low testosterone does not result from a defect in the hypothalamus or pituitary; (2) a lack of correlation between estrogen and insulin sensitivity; and (3) that effects of low testosterone on insulin sensitivity, if any, are mediated through changes in body mass index (BMI).

In one embodiment of the present invention, administration of a composition comprising an effective amount of an antiestrogen is used to treat metabolic syndrome in a subject in need of such treatment. The subject may be a male or female. The subject may also have idiopathic or secondary hypogonadotrophic hypogonadism.

In a preferred embodiment of the present invention, a composition comprising an effective amount of trans-clomiphene or a predefined blend of the isomers of clomiphene as described below differing from the normally produced mixture, is used to treat metabolic syndrome in a male or female subject.

It is to be understood that where the term "metabolic syndrome" is used herein, this relates to metabolic syndrome as defined by the Adult Treatment Panel or any other recognized definition of this syndrome. Synonyms for "metabolic syndrome" used in the art include Reaven's Syndrome, Insulin Resistance Syndrome and Syndrome X. It is to be understood that where the term "metabolic syndrome" is used herein it also refers to Reaven's Syndrome, Insulin Resistance Syndrome and Syndrome X.

In another embodiment of the present invention, administration of a composition comprising an effective amount of an antiestrogen, preferably trans-clomiphene, is used to treat a symptom of metabolic syndrome in a subject in need of such treatment. The symptom of metabolic syndrome may include, without limitation, elevated glucose levels, elevated triglyceride levels, elevated cholesterol levels, insulin resistance, high blood pressure, abdominal obesity, prothrombotic state, proinflammatory state, or any combination of two or more symptoms. The subject may be male or female. The subject may also have idiopathic or secondary hypogonadotrophic hypogonadism.

In another embodiment of the present invention, administration of a composition comprising an effective amount of an antiestrogen, preferably trans-clomiphene, to a subject with metabolic syndrome may be combined with any known treatment regimen. Known treatment regimens for metabolic syndrome include, without limitation, exercise regimens, weight reduction regimens, blood pressure medications such as ACE inhibitors, cholesterol reducing medications, and metformin. Compositions of the invention may be simultaneously, separately or sequentially administered with any of the aforementioned known treatment regimens.

In another embodiment of the present invention, administration of a composition comprising an effective amount of an antiestrogen is used to treat impaired fasting glucose in a subject. The subject may be male or female. The subject may have idiopathic or secondary hypogonadotrophic hypogonadism.

It is to be understood that "impaired fasting glucose" as used herein is defined with respect to the fasting blood glucose tolerance test. In this test, a subject's blood glucose is measured after fasting for 8 to 12 hours. A person with normal fasting glucose has a fasting blood glucose level below 110 mg/dl. A person with impaired fasting glucose has a fasting blood glucose level between 110 mg/dl and 125 mg/dl. A fasting glucose level higher than 125 mg/dl indicates diabetes. Accordingly, compositions of the instant invention may be administered to a subject with fasting blood glucose levels between 110 mg/dl and 125 mg/dl. For example, the subject may have a fasting blood glucose level of 110, 111, 112, 113, 114, 115, 116, 117, 118, 119, 120, 121, 122, 123, 124, or 125 mg/dl.

Administration of compositions of the invention may decrease fasting blood glucose levels to below 125, 124, 123, 122, 121, 120, 119, 118, 117, 116, 115, 114, 113, 112, 111 and preferably below 110 mg/dl.

Patients with impaired fasting glucose have a significant risk of developing diabetes. Accordingly, the present invention provides a method for preventing the transition from impaired fasting glucose to diabetes mellitus in a subject comprising the administration to the subject of a composition comprising an effective amount of an antiestrogen, preferably trans-clomiphene. The subject may be male or female. The subject may also have idiopathic or secondary hypogonadal hypogonadism.

In another embodiment of the present invention, a patient with idiopathic or secondary hypogonadotrophic hypogonadism with a need or desire to lower fasting blood glucose levels is administered a composition comprising an effective amount of an antiestrogen, preferably trans-clomiphene. The hypogonadal patient may have any fasting glucose level, but preferably has a fasting glucose level above about 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 160, 165, 170, 175, 180, 185, 190, 195, or 200 mg/dl. For example, the hypogonadal patient may have fasting glucose levels between 125 and 140 mg/dl. The composition may comprise an amount of an antiestrogen, preferably trans-clomiphene, to lower the hypogonadal patient's fasting glucose level below 200, 195, 190, 185, 180, 175, 170, 165, 160, 155, 154, 153, 152, 151, 150, 149, 148, 147, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111 or preferably below 110 mg/dl.

Where the hypogonadal patient's glucose level is above about 125 mg/dl, the patient may also be diagnosed with diabetes mellitus type 2. Thus, the present invention also provides a method for treating diabetes mellitus type 2 comprising administering to a subject in need thereof, a composition comprising an effective amount of an antiestrogen, preferably trans-clomiphene, or a pharmaceutically acceptable salt thereof. In this regard, compositions of the invention may be may be combined with any known treatment regimen for diabetes mellitus type 2. Known treatment regimens for diabetes mellitus type 2 include, without limitation: exercise regimens; weight reduction regimens; blood pressure medications such as angiotensin-converting enzyme (ACE) inhibitors (e.g. ramipril); metformin; thiazolidinediones (TZDs); α-glucosidase inhibitors such as acarbose and miglitol; meglitinides such as nateglinide, repaglinide; peptide analogs such as dipeptidyl peptidase-4 (DPP-4) inhibitors and amylin agonist analogs; and insulin. Compositions of the invention may be simultaneously, separately or sequentially administered with any of the aforementioned known treatment regimens.

Subjects in need of treatment by any of the methods of the present invention may have low or low-normal total testosterone. For example, male subjects in need of treatment may have total testosterone levels below about 320, 310, 300, 295, 290, 285, 280, 275, 270, 265, 260, 255, 250, 245, 240, 235, 230, 225, 220, 215, 210, 205, 200, 195, 190, 185, 180, 175, 170, 165, 160, 155, 150, 145, 140, 135, 130, 125, 120, 115, 105, 100, 95, 90, 85, 80, 75, 70, 65, 60, 55, 50, 45, 40, 35, 30, 25, 20, 15, 10 or 5 ng/dl. Male subjects with total testosterone below about 300 ng/dl are defined as hypogonadal.

In a related aspect, the present invention provides a method for treating adult onset idiopathic hypogonadotrophic hypogonadism (AIHH) or a condition associated therewith, comprising administering to a subject in need thereof an effective amount of a composition comprising an antiestrogen, preferably trans-clomiphene or a salt thereof. Men with AIHH are characterized as having both low testosterone and luteinizing hormone (LH) often accompanied by, inter alia, obesity and elevated blood glucose. Compositions of the invention may be useful in treating any of these conditions.

In a preferred embodiment of the present invention, a patient with idiopathic or secondary hypogonadotrophic hypogonadism who has developed metabolic syndrome is administered one or more dosages of an effective amount of a composition comprising trans-clomiphene at a dosage between one mg to about 200 mg (although the determination of optimal dosages is within the level of ordinary skill in the art) in order to treat metabolic syndrome or a condition associated therewith. Cis-clomiphene may also be present in the composition so long as the ratio of trans-clomiphene to cis-clomiphene is greater than 71/29. Analogs of the trans- and cis-isomers of clomiphene such as those described in Ernst, et al. supra are also useful in the practice of the present invention.

Dosages are preferably (but not necessarily) administered as part of a dosage regimen designed to give rise to serum testosterone levels that mimic or correspond to the normal secretary total serum testosterone profile described in FIG. 1 during the period of administration and preferably during the period of discontinuance as well. For example, according to FIG. 1 a dosage of the preferred composition may be administered in a pharmaceutical formulation that would give rise to peak serum testosterone levels at around 8 a.m. Such pharmaceutical formulations may be in the form of sustained release formulations prepared as described for example in U.S. Pat. No. 6,221,399, Japanese patent 4-312522, Meshali et al, Int. J. Phar. 89:177-181 (1993), Kharenko et al, Intern. Symp. Control Rel. Bioact. Mater. 22:232-233 (1995), WO 95/35093, Dangprasit et al., Drug. Devel. and Incl. Pharm. 21 (20):2323-2337 (1995); U.S. Pat. Nos. 6,143,353, 6,190,591, 6,096,338, 6,129,933, 6,126,969, 6,248,363 and other sustained release formulations well known in the art. The dosage of trans-clomphene may be from 5 to 100 mg. The dosage of trans-clomphene may also be from 12.5 to 50 mg. The dosage of trans-clomphene may also be 12.5 mg, 25 mg or 50 mg.

The terms "treat" or "treatment" as used in the instant application, refer to both therapeutic treatment and prophylactic or preventative measures, wherein the object is to prevent or slow down (lessen) an undesired physiological or psychological change or disorder, such as conditions associated with metabolic syndrome. For purposes of the present invention, beneficial or desired clinical results include, but are not limited to, alleviation of symptoms, diminishment of extent of disease, stabilized (i.e., not worsening) state of disease, delay or slowing of disease progression, amelioration or palliation of the disease state and remission (whether partial or total), whether detectable or undetectable. "Treatment" can also mean prolonging survival as compared to expected survival if not receiving treatment. Individuals in need of treatment include those already with the condition or disorder as well as those prone to develop the condition or disorder or those in whom the condition or disorder is to be prevented.

The terms "modulate" or "modulating", as used in the instant application, refer to both therapeutic treatment and prophylactic or preventative measures, wherein the object is to prevent or slow down (lessen) an undesired clinical parameter. For purposes of the present invention, beneficial or desired clinical results include, but are not limited to, correcting of clinical parameter, diminishment of extent of clinical parameter, stabilized (i.e., not worsening) clinical parameter and delay or slowing of extent of clinical parameter.

By "antiestrogen" it is meant a compound that prevents estrogens from expressing their effects on estrogen dependent target tissues consequently antagonizing a variety of estrogen-dependent processes. Based on the unexpected finding that the antiestrogenic trans-clomiphene isomer is useful in treating metabolic syndrome in hypogonadal subjects, it is expected that compounds with antiestrogenic activity will be useful in the present invention. In all cases, antiestrogens useful in the practice of the instant invention are those capable of elevating testosterone levels in a mammal. Without wishing to be bound by theory, it is believed that administration of antiestrogens will result in elevated testosterone levels by blocking the negative feedback exerted by normal estrogens on the pituitary leading to increases in LH and FSH. In men, these increased levels of gonadotropins stimulate the Leydig cells of the testes and result in the production of higher testosterone levels.

Antiestrogens useful in the practice of the instant invention may be pure antiestrogens or may have partial estrogenic action as in the case of the selective estrogen receptor modulators (SERMs) which exhibit antiestrogenic properties in some tissues and estrogenic tissues in others.

Pure antiestrogens of the invention include, without limitation: RU 58,688, described in Van de Velde et al., Ann. NY Acad. Sci., 761(3):164-175 (1995); 13-methyl-7-[9-(4,4,5,5, 5-pentafluoropentylsulfinyl)nonyl]-7,8,9,11,12,13,14,15,16, 17-decahydro-6H-cyclopenta[a]-phenanthrene-3,17-diol (ICI 182,780/fulvestrant) and other compounds described in EP 0138504; N-butyl-11-[(7R,8S,9S,13S,14S,17S)-3,17-dihydroxy-13-methyl-6,7,8,9,11,12,14,15,16,17-decahydro-cyclopena[a]phenanthren-7-yl]-N-methyl-undecanamide (ICI 164,384), described in Wakeling and Bowler, J. Endocrin., 112:R7-R110 (1987); (#)-7-pivaloyloxy-3-(4'pivaloyloxyphenyl)-4-methyl-2-(4"-(2"piperidinoethoxy)phenyl)-2H-benzopyran (EM-800/SCH 57050) and other compounds described in WO 96/26201; (2S)-3-(4-hydroxyphenyl)-4-methyl-2-[4-[2-(1-piperidyl)ethoxy]phenyl]-2H-chromen-7-ol (EM-652/SCH 57068) and the like.

SERMs of the invention include, without limitation, triphenylalkylenes such as triphenylethylenes, which include: 2-[4-(1,2-diphenylbut-1-enyl)phenoxy]-N,N-dimethyl-ethanamine (tamoxifen) and other compounds described in U.S. Pat. No. 4,536,516, incorporated herein by reference; Trans-4-(1-(4-(2-dimethylamino)ethoxy)phenyl)-2-phenyl-1-butenyl)phenol (4-hydroxytamoxifen) and other compounds described in U.S. Pat. No. 4,623,660, incorporated herein by reference; 1-[4'-dimethylaminoethoxy)phenyl]-1-(3'-hydroxyphenyl)-2-phenylbut-1-ene (droloxifene) and other compounds described in U.S. Pat. No. 5,047,431, incorporated herein by reference; 2-[p-[(Z)-4-chloro-1,2-diphenyl-1-butenyl]phenoxy]-N,N-dimethylethylamine (toremifene) and other compounds described in U.S. Pat. Nos. 4,696,949, 5,491,173 and 4,996,225, each of which is incorporated herein by reference; (E)-1-(2-(4-(1-(4-iodo-phenyl)-2-phenyl-but-1-enyl)-phenoxy)-ethyl)-pyrrol idinone (idoxifene) and other compounds described in U.S. Pat. No. 4,839,155, incorporated herein by reference; clomiphene and both its isomers; and compounds described in U.S. Pat. Nos. 4,696, 949 and 5,491,173 and 6,576,645, each of which is incorporated herein by reference.

SERMS of the invention also include, without limitation, benzothiphene derivatives such as: [6-hydroxy-2-(4-hydroxyphenyl)-benzothiophen-3-yl]-[4-[2-(1-piperidinyl)ethoxy) phenyl]-methanone (raloxifene) and other compounds described in U.S. Pat. Nos. 4,418,068 and 5,393,763, both of which are incorporated herein by reference; LY353381; and LY335563 and other compounds described in WO 98/45286, WO 98/45287 and WO 98/45288; benzopyran derivatives such as: (#)-7-pivaloyloxy-3-(4'pivaloyloxyphenyl)-4-methyl-2-(4"-(2"piperidinoethoxy)phenyl)-2H-benzopyran (EM 800/SCH 57050) and other compounds described in WO 96/26201; (2S)-3-(4-hydroxyphenyl)-4-methyl-2-[4-[2-(1-piperidyl)ethoxy]phenyl]-2H-chromen-7-ol (EM 652); naphthalene derivatives such as: Cis-6-phenyl-5-[4-(2-pyrrolidin-1-yl-ethoxy)-phenyl]-5,6,7,8-tetrahydronaphthalen-2-ol (lasofoxifene/CP 336,156) and other compounds described in U.S. Pat. Nos. 5,552,412; 3,4-dihydro-2-(p-methoxyphenyl)-1-naphthyl-p-[2-(1-pyrrolidinyl)ethoxy]phenyl ketone (trioxifene/LY133314) and other compounds described in U.S. Pat. No. 4,230,862, incorporated herein by reference; and 1-(4-Substituted alkoxy)benzyl)naphthalene compounds such as those described in U.S. Pat. No. 6,509,356, incorporated herein by reference; chromans such as 3,4-trans-2,2-dimethyl-3-phenyl-4-[4-(2-(2-(pyrrolidin-1-yl)ethoxy)phenyl]-7-methoxychroman (levormeloxifene) and other compounds described in WO 97/25034, WO 97/25035, WO 97/25037 and WO 97/25038; and 1-(2-((4-(-methoxy-2,2,dimethyl-3-phenyl-chroman-4-yl)-phenoxy)-ethyl)-pyrrolidine (centchroman) and other compounds described in U.S. Pat. No. 3,822,287, incorporated herein by reference.

Other SERMs of the invention include, without limitation, the compounds described in U.S. Pat. Nos. 6,387,920, 6,743,815, 6,750,213, 6,869,969, 6,927,224, 7,045,540, 7,138,426, 7,151,196, and 7,157,604, each of which is incorporated herein by reference.

Further non-limiting antiestrogens of the invention include: 6α-chloro-16α-methyl-pregn-4-ene-3,20-dione (clometherone); 6-chloro-17-hydroxypregna-1,4,6-triene-3,20-dione (delmadinone); 1-[2-[4-[1-(4-methoxyphenyl)-2-nitro-2-phenylethenyl]phenoxy]ethyl]-pyrrolidine (nitromifene/CN-55,945-27); and 1-[2-[p-(3,4-Dihydro-6-methoxy-2-phenyl-1-naphthyl)phenoxy]ethyl]pyrrolidine (nafoxidene).

Further non-limiting antiestrogens of the invention include indoles such as those disclosed in J. Med. Chem., 33:2635-2640 (1990), J. Med. Chem., 30:131-136 (1987), WO 93/10741, WO 95/17383, WO 93/23374 and U.S. Pat. Nos. 6,503,938 and 6,069,153, both of which are incorporated herein by reference.

Further non-limiting antiestrogens of the invention include 2-[3-(1-cyano-1-methyl-ethyl)-5-(1H-1,2,4-triazol-1-ylmethyl)phenyl]-2-methyl-propanenitrile (anastrozole) and other compounds described in EP 0296749; 6-Methylenandrosta-1,4-diene-3,17-dione (exemestane) and other compounds described in U.S. Pat. No. 4,808,616, incorporated herein by reference; 4-[(4-cyanophenyl)-(1,2,4-triazol-1-yl)methyl]benzonitrile (letrozole) and other compounds described in U.S. Pat. No. 5,473,078, incorporated herein by reference; 1-[4'-dimethylaminoethoxy)phenyl]-1-(3'-hydroxyphenyl)-2-phenylbut-1-ene (droloxifene) and other compounds described in U.S. Pat. No. 5,047,431, incorporated herein by reference; 2α,3α-Epithio-5α-androstan-17β-ol (epitiostanol); 2α,3α-Epitio-5α-androstane-17β-yl-1-methoxycyclopentyloxy (mepitiostane); 4-[(2Z,4Z)-4-(4-hydroxyphenyl)hexa-2,4-dien-3-yl]phenol (cycladiene) and other compounds described in U.S. Pat. Nos. 2,464,203 and 2,465,505, both of which are incorporated herein by reference; CI-680 described in Unlisted Drugs, 28(10): 169(O) (1976); CI-628 described in Unlisted Drugs, 26(7): 106(1) (1974); 13-ethyl-17α-ethynl-17β-hydroxygona-4,9,1-trien-3-one (R2323); diphenol hydrochrysene and erythyro-MEA both described in Geynet, et al., Gynecol. Invest. 3(1):2-29 (1972); 1-[1-chloro-2,2-bis(4-methoxyphenyl)ethenyl]-4-methoxy-benzene (chlorotrianisene) described in Merck Index, 10$^{th}$ ed., #2149; 1-[4-(2-Diethylaminoethoxy)phenyl]-1-phenyl-2-(p-anisyl)ethanol (ethamoxytriphetol) described in Merck Index, 10$^{th}$ ed., #3668; and 2-p-Chlorophenyl-1-[p-(2-diethylaminoethoxy)phenyl]-1-p-tolylethanol (triparanol) and other compounds described in U.S. Pat. No. 2,914,562, incorporated herein by reference.

Still other antiestrogens of the invention include, without limitation: (2e)-3-(4-((1e)-1,2-diphenylbut-1-enyl)phenyl) acrylic acid (GW5638), GW7604 and other compounds described in Wilson et al., Endocrinology, 138(9):3901-3911 (1997) and WO 95/10513; 1-[4-(2-diethylaminoethoxy)phenyl]-2-(4-methoxyphenyl)-1-phenyl-ethanol (MER-25), N,N-diethyl-2-[4-(5-methoxy-2-phenyl-3H-inden-1-yl)phenoxy]ethanamine hydrochloride (U-11,555A), 1-[2-[4-(6-methoxy-2-phenyl-3,4-dihydronaphthalen-1-yl)phenoxy]ethyl]pyrrolidine hydrochloride (U-11,100A), ICI-46,669, 2-[4-[(Z)-1,2-diphenylbut-1-enyl]phenoxy]-N,N-dimethylethanamine; 2-hydroxypropane-1,2,3-tricarboxylic acid (ICI-46,474) and other compounds described in Terenius et al., Gynec. Invest., 3:96-107 (1972); 2-Hydroxy-6-naphthalenepropionic acid (allenolic acid); [4-[(4-acetyloxyphenyl)-cyclohexylidene-methyl]phenyl]acetate (cyclofenyl/ICI-48213); [6-hydroxy-2-(4-hydroxyphenyl)benzothiophen-3-yl]-[4-[2-(1-piperidyl)ethoxy]phenyl]methanone (keoxifene); 4-[(Z)-1-[4-(2-dimethylaminoethoxy)phenyl]-2-(4-propan-2-ylphenyl)but-1-enyl]phenol (DP-TAT-59/miproxifene); (1RS,2RS)-4,4'-diacetoxy-5,5'-difluoro-(1-ethyl-2-methylene)di-m-phenylenediacetate (acefluranol); 6-hydroxy-2-(p-hydroxyphenyl)-benzo[b]thien-3-yl[2-(1-pyrrolidinyl)-ethoxyphenyl]ketone (LY-117018); and [6-hydroxy-2-(4-hydroxy-phenyl)benzo(b)thien-3-yl]-[4-(2-(1-piperidinyl)-ethoxy)phenyl]methanone (LY-156758).

Still other antiestrogens of the invention include, without limitation: non-steroidal estrogen receptor ligands such as those described in U.S. Pat. Nos. 5,681,835, 5,877,219, 6,207,716, 6,340,774 and 6,599,921, each of which is incorporated herein by reference; steroid derivatives such as those described in U.S. Pat. No. 4,659,516, incorporated herein by reference; 7α-11-aminoalkyl-estratrienes such as those described in WO 98/07740; 11-(β-halogen-7α-substituted estratrienes such as those described in WO 99/33855; 17α-alkyl-17β-oxy-estratrienes such as those described in U.S. patent application Ser. No. 10/305,418, incorporated herein by reference; 2-phenyl-1-[4-(2-aminoethoxy)-benzyl]-indoles such as those described in U.S. Pat. No. 7,132,417, incorporated herein by reference; 4-fluoroalkyl-2h-benzopryans such as those described in U.S. Pat. No. 6,844,336, incorporated herein by reference; (4-(2-(2-aza-bicyclo[2.2.1]hept-2-yl)-ethoxy)-phenyl)-(6-hydroxy-2-(4-hydroxy-phenyl)-benzo[b]thiop hen-3-yl)-methanone and other benzothiophenes described in WO 95/10513 and U.S. Pat. No. 4,133,814, incorporated herein by reference; 2-phenyl-1-[4-(2-aminoethoxy)-benzyl]-indoles such as those described in U.S. Pat. No. 5,998,402, incorporated herein by reference; 3-[4-(2-Phenyl-Indole-1-ylmethyl)Phenyl]-Acrylamides and other compounds described in U.S. Pat. No. 5,985,910, incorporated herein by reference; 2-phenyl-1-[4-(amino-1-yl-alk-1-ynyl)-benzyl]-1H-indol-5-ols and other compounds described in U.S. Pat. Nos. 5,780,497 and 5,880,137, both of which are incorporated herein by reference; steroids such as those described in U.S. Pat. Nos. 6,455,517, 6,548,491, 6,747,018 and 7,041,839, each of which is incorporated herein by reference; Di-(3'-hydroxyphenyl)-alkane compounds such as those described in U.S. Pat. No. 4,094,994, incorporated herein by reference; phenol derivatives such as those described in U.S. Pat. No. 4,751,240, incorporated herein by reference; 2,3-diaryl-2H-1-benzopyran analogs such as those described in Saeed et al., J. Med. Chem., 33:3210-3216 (1990) and Sharma et al., J. Med. Chem. 33:3216-3229 (1990); and benzofuran and triarylfuran analogs such as those described in Durani et al., J. Med. Chem., 32:1700-1707 (1989).

In one embodiment, compositions of the invention comprise one or more antiestrogens or pharmaceutically acceptable salts thereof. Depending on the process conditions the salt compound obtained may be either in neutral or salt form. Salt forms include hydrates and other solvates and also crystalline polymorphs. Both the free base and the salts of these end products may be used in accordance with the invention.

Acid addition salts may in a manner known per se be transformed into the free base using basic agents such as alkali or by ion exchange. The free base obtained may also form salts with organic or inorganic acids.

In the preparation of acid addition salts, preferably such acids are used which form suitably pharmaceutically acceptable salts. Examples of such acids are hydrochloric acid, sulfuric acid, phosphoric acid, nitric acid, aliphatic acid, alicyclic carboxylic or sulfonic acids, such as formic acid, acetic acid, propionic acid, succinic acid, glycolic acid, lactic acid, malic acid, tartaric acid, citric acid, ascorbic acid, glucuronic acid, fumaric acid, maleic acid, hydroxymaleic acid, pyruvic acid, aspartic acid, glutamic acid, p-hydroxybenzoic acid, embonic acid, ethanesulfonic acid, hydroxyethanesulfonic acid, phenylacetic acid, mandelic acid, alogenbensenesulfonic acid, toluenesulfonic acid, galactaric acid, galacturonic acid or naphthalenesulfonic acid. All crystalline form polymorphs may be used in accordance with the invention.

Base addition salts may also be used in accordance with the invention and may be prepared by contacting the free acid form with a sufficient amount of the desired base to produce the salt in the conventional manner. The free acid form may be regenerated by contacting the salt form with an acid and isolating the free acid in the conventional manner. Pharmaceutically acceptable base addition salts are formed with metals or amines, such as alkali and alkali earth metals or organic amines. Examples of metals used as cations are sodium, potassium, calcium, magnesium and the like. Examples of suitable amines are amino acids such as lysine, choline, diethanolamine, ethylenediamine, N-methylglucamine and the like.

Compositions of the instant invention can be prepared in the form of a dose unit or dose units suitable for oral, parenteral, transdermal, rectal, transmucosal, or topical administration. Parenteral administration includes, but is not limited to, intravenous, intraarterial, intraperitoneal, subcutaneous, intramuscular, intrathecal, and intraarticular.

The terms "oral administration" or "orally deliverable" herein include any form of delivery of a therapeutic agent or a composition thereof to a subject wherein the agent or composition is placed in the mouth of the subject, whether or not the agent or composition is swallowed. Thus, "oral administration" includes buccal and sublingual as well as esophageal (e.g. inhalation) administration.

In still another embodiment, compositions of the present invention are formulated as rectal suppositories, which may contain suppository bases including, but not limited to, cocoa butter or glycerides.

Compositions of the present invention may also be formulated for inhalation, which may be in a form including, but not limited to, a solution, suspension, or emulsion that may be administered as a dry powder or in the form of an aerosol using a propellant, such as dichlorofluoromethane or trichlorofluoromethane.

Compositions of the present invention may also be formulated for transdermal delivery, for example as a cream, ointment, lotion, paste, gel, medicated plaster, patch, or membrane. Such compositions can comprise any suitable excipients, for example penetration enhancers and the like.

Compositions of the present invention may also be formulated for parenteral administration including, but not limited to, by injection or continuous infusion. Formulations for injection may be in the form of suspensions, solutions, or emulsions in oily or aqueous vehicles. Such compositions may also be provided in powder form for reconstitution with a suitable vehicle including, but not limited to, sterile, pyrogen-free water, WFI, and the like.

Compositions of the present invention may also be formulated as a depot preparation, which may be administered by implantation or by intramuscular injection. Such compositions may be formulated with suitable polymeric or hydrophobic materials (as an emulsion in an acceptable oil, for example), ion exchange resins, or as sparingly soluble derivatives (as a sparingly soluble salt, for example).

Compositions of the present invention may also be formulated as a liposome preparation. Liposome preparations can comprise liposomes which penetrate the cells of interest or the stratum corneum and fuse with the cell membrane resulting in delivery of the contents of the liposome into the cell. For example, liposomes such as those described in U.S. Pat. No. 5,077,211 to Yarosh, U.S. Pat. No. 4,621,023 to Redziniak et al., or U.S. Pat. No. 4,508,703 to Redziniak et al., can be used.

A composition of the invention can be in the form of solid dosage units such as tablets, (e.g. suspension tablets, bite suspension tablets, rapid dispersion tablets, chewable tablets, effervescent tablets, bilayer tablets, etc.), caplets, capsules (e.g., a soft or a hard gelatin capsule), powder (e.g. a packaged powder, a dispensable powder or an effervescent powder), lozenges, sachets, cachets, troches, pellets, granules, microgranules, encapsulated microgranules, powder aerosol formulations, or any other solid dosage form reasonably adapted for administration.

Tablets can be prepared according to any of the many relevant, well known pharmacy techniques. In one embodiment, tablets or other solid dosage forms can be prepared by processes that employ one or a combination of methods including, without limitation, (1) dry mixing, (2) direct compression, (3) milling, (4) dry or non-aqueous granulation, (5) wet granulation, or (6) fusion.

The individual steps in the wet granulation process of tablet preparation typically include milling and sieving of the ingredients, dry powder mixing, wet massing, granulation and final grinding. Dry granulation involves compressing a powder mixture into a rough tablet or "slug" on a heavy-duty rotary tablet press. The slugs are then broken up into granular particles by a grinding operation, usually by passage through an oscillation granulator. The individual steps include mixing of the powders, compressing (slugging) and grinding (slug reduction or granulation). Typically, no wet binder or moisture is involved in any of the steps.

In another embodiment, solid dosage forms can be prepared by mixing an antiestrogen with one or more pharmaceutical excipients to form a substantially homogenous preformulation blend. The preformulation blend can then be subdivided and optionally further processed (e.g. compressed, encapsulated, packaged, dispersed, etc.) into any desired dosage forms.

Compressed tablets can be prepared by compacting a powder or granulation composition of the invention. The term "compressed tablet" generally refers to a plain, uncoated tablet suitable for oral ingestion, prepared by a single compression or by pre-compaction tapping followed by a final compression. Tablets of the present invention may be coated or otherwise compounded to provide a dosage form affording the advantage of improved handling or storage characteristics. In one embodiment, any such coating will be selected so as to not substantially delay onset of therapeutic effect of a composition of the invention upon administration to a subject. The term "suspension tablet" as used herein refers to a compressed tablet that rapidly disintegrates after placement in water.

Suitable liquid dosage forms of a composition of the invention include solutions, aqueous or oily suspensions, elixirs, syrups, emulsions; liquid aerosol formulations, gels, creams, ointments, etc. Such compositions may also be formulated as a dry product for constitution with water or other suitable vehicle before use.

In one embodiment, liquid or semi-solid compositions, upon storage in a closed container maintained at either room temperature, refrigerated (e.g. about 5-10° C.) temperature, or freezing temperature for a period of about 1, 2, 3, 4, 5, 6, 7, 8, 9, 10, 11, or 12 months, exhibit at least about 90%, at least about 92.5%, at least about 95%, or at least about 97.5% of the original antiestrogen compound present therein.

Compositions of the invention can, if desired, include one or more pharmaceutically acceptable excipients. The term "excipient" herein means any substance, not itself a therapeutic agent, used as a carrier or vehicle for delivery of a therapeutic agent to a subject or added to a pharmaceutical composition to improve its handling or storage properties or to permit or facilitate formation of a unit dose of the composition. Excipients include, by way of illustration and not limitation, diluents, disintegrants, binding agents, adhesives, wetting agents, lubricants, glidants, surface modifying agents or surfactants, fragrances, suspending agents, emulsifying agents, nonaqueous vehicles, preservatives, antioxidants, adhesives, agents to adjust pH and osmolarity (e.g. buffering agents), preservatives, thickening agents, sweetening agents, flavoring agents, taste masking agents, colorants or dyes, penetration enhancers and substances added to improve appearance of the composition.

Excipients optionally employed in compositions of the invention can be solids, semi-solids, liquids or combinations thereof. Compositions of the invention containing excipients can be prepared by any known technique of pharmacy that comprises mixing an excipient with a drug or therapeutic agent.

Compositions of the invention optionally comprise one or more pharmaceutically acceptable diluents as excipients. Suitable diluents illustratively include, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of α- and amorphous cellulose (e.g., Rexcel™) and powdered cellulose; calcium carbonate; glycine; bentonite; polyvinylpyrrolidone; and the like. Such diluents; if present, constitute in total about 5% to about 99%, about 10% to about 85%, or about 20% to about 80%, of the total weight of the composition. Any diluent or diluents selected preferably exhibit suitable flow properties and, where tablets are desired, compressibility.

The use of extragranular microcrystalline cellulose (that is, microcrystalline cellulose added to a wet granulated composition after a drying step) can be used to improve hardness (for tablets) and/or disintegration time.

Compositions of the invention optionally comprise one or more pharmaceutically acceptable disintegrants as excipients, particularly for tablet, capsule or other solid formulations. Suitable disintegrants include, either individually or in combination, starches, including sodium starch glycolate (e.g., Explotab™ of PenWest) and pregelatinized corn starches (e.g., National™ 1551, National™ 1550, and Colocorn™ 1500), clays (e.g., Veegum™ HV), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, xanthan, locust bean, karaya, pectin and tragacanth gums.

Disintegrants may be added at any suitable step during the preparation of the composition, particularly prior to a granulation step or during a lubrication step prior to compression. Such disintegrants, if present, constitute in total about 0.2% to about 30%, about 0.2% to about 10%, or about 0.2% to about 5%, of the total weight of the composition.

Compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™); and ethylcellulose (e.g., Ethocel™). Such binding agents and/or adhesives, if present, constitute in total about 0.5% to about 25%, about 0.75% to about 15%, or about 1% to about 10%, of the total weight of the composition.

Compositions of the invention optionally comprise one or more pharmaceutically acceptable wetting agents as excipients. Non-limiting examples of surfactants that can be used as wetting agents in compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefossé), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefossé), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, about 0.4% to about 10%, or about 0.5% to about 5%, of the total weight of the composition.

Compositions of the invention optionally comprise one or more pharmaceutically acceptable lubricants (including antiadherents and/or glidants) as excipients. Suitable lubricants include, either individually or in combination, glyceryl behapate (e.g., Compritol™ 888); stearic acid and salts thereof, including magnesium (magnesium stearate), calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, about 0.2% to about 8%, or about 0.25% to about 5%, of the total weight of the composition.

Suitable anti-adherents include talc, cornstarch, DL-leucine, sodium lauryl sulfate and metallic stearates. Talc is an anti-adherent or glidant used, for example, to reduce formulation sticking to equipment surfaces and also to reduce static in the blend. One or more anti-adherents, if present, constitute about 0.1% to about 10%, about 0.25% to about 5%, or about 0.5% to about 2%, of the total weight of the composition.

Glidants can be used to promote powder flow of a solid formulation. Suitable glidants include colloidal silicon dioxide, starch, talc, tribasic calcium phosphate, powdered cellulose and magnesium trisilicate. Colloidal silicon dioxide is particularly preferred.

Compositions of the present invention can comprise one or more anti-foaming agents. Simethicone is an illustrative anti-foaming agent. Anti-foaming agents, if present, constitute about 0.001% to about 5%, about 0.001% to about 2%, or about 0.001% to about 1%, of the total weight of the composition.

Illustrative antioxidants for use in the present invention include, but are not limited to, butylated hydroxytoluene, butylated hydroxyanisole, potassium metabisulfite, and the like. One or more antioxidants, if desired, are typically present in a composition of the invention in an amount of about 0.01% to about 2.5%, for example about 0.01%, about 0.05%, about 0.1%, about 0.5%, about 1%, about 1.5%, about 1.75%, about 2%, about 2.25%, or about 2.5%, by weight.

In various embodiments, compositions of the invention can comprise a preservative. Suitable preservatives include, but are not limited to, benzalkonium chloride, methyl, ethyl, propyl or butylparaben, benzyl alcohol, phenylethyl alcohol, benzethonium, methyl or propyl p-hydroxybenzoate and sorbic acid or combinations thereof. Typically, the optional preservative is present in an amount of about 0.01% to about 0.5% or about 0.01% to about 2.5%, by weight.

In one embodiment, compositions of the invention optionally comprise a buffering agent. Buffering agents include agents that reduce pH changes. Illustrative classes of buffering agents for use in various embodiments of the present invention comprise a salt of a Group IA metal including, for example, a bicarbonate salt of a Group IA metal, a carbonate salt of a Group IA metal, an alkaline or alkali earth metal buffering agent, an aluminum buffering agent, a calcium buffering agent, a sodium buffering agent, or a magnesium buffering agent. Suitable buffering agents include carbonates, phosphates, bicarbonates, citrates, borates, acetates, phthalates, tartrates, succinates of any of the foregoing, for example sodium or potassium phosphate, citrate, borate, acetate, bicarbonate and carbonate.

Non-limiting examples of suitable buffering agents include aluminum, magnesium hydroxide, aluminum glycinate, calcium acetate, calcium bicarbonate, calcium borate, calcium carbonate, calcium citrate, calcium gluconate, calcium glycerophosphate, calcium hydroxide, calcium lactate, calcium phthalate, calcium phosphate, calcium succinate, calcium tartrate, dibasic sodium phosphate, dipotassium hydrogen phosphate, dipotassium phosphate, disodium hydrogen phosphate, disodium succinate, dry aluminum hydroxide gel, magnesium acetate, magnesium aluminate, magnesium borate, magnesium bicarbonate, magnesium carbonate, magnesium citrate, magnesium gluconate, magnesium hydroxide, magnesium lactate, magnesium metasilicate aluminate, magnesium oxide, magnesium phthalate, magnesium phosphate, magnesium silicate, magnesium succinate, magnesium tartrate, potassium acetate, potassium carbonate, potassium bicarbonate, potassium borate, potassium citrate, potassium metaphosphate, potassium phthalate, potassium phosphate, potassium polyphosphate, potassium pyrophosphate, potassium succinate, potassium tartrate, sodium acetate, sodium bicarbonate, sodium borate, sodium carbonate, sodium citrate, sodium gluconate, sodium hydrogen phosphate, sodium hydroxide, sodium lactate, sodium phthalate, sodium phosphate, sodium polyphosphate, sodium pyrophosphate, sodium sesquicarbonate, sodium succinate, sodium tartrate, sodium tripolyphosphate, synthetic hydrotalcite, tetrapotassium pyrophosphate, tetrasodium pyrophosphate, tripotassium phosphate, trisodium phosphate, and trometamol. (Based in part upon the list provided in The Merck Index, Merck & Co. Rahway, N.J. (2001)). Furthermore, combinations or mixtures of any two or more of the above mentioned buffering agents can be used in the pharmaceutical compositions described herein. One or more buffering agents, if desired, are present in compositions of the invention in an amount of about 0.01% to about 5% or about 0.01% to about 3%, by weight.

In various embodiments, compositions the invention may include one or more agents that increase viscosity. Illustrative agents that increase viscosity include, but are not limited to, methylcellulose, carboxymethylcellulose sodium, ethylcellulose, carrageenan, carbopol, and/or combinations thereof. Typically, one or more viscosity increasing agents, if desired, are present in compositions of the invention in an amount of about 0.1% to about 10%, or about 0.1% to about 5%, by weight.

In various embodiments, compositions of the invention comprise an "organoleptic agent" to improve the organoleptic properties of the composition. The term "organoleptic agent" herein refers to any excipient that can improve the flavor or odor of, or help mask a disagreeable flavor or odor of a composition of the invention. Such agents include sweeteners, flavoring agents and/or taste masking agents. Suitable sweeteners and/or flavoring agents include any agent that sweetens or provides flavor to a pharmaceutical composition. Optional organoleptic agents are typically present in a composition of the invention in an amount of about 0.1 mg/ml to about 10 mg/ml, about 0.5 mg/ml to 5 mg/ml or about 1 mg/ml.

Illustrative sweeteners or flavoring agents include, without limitation, acacia syrup, anethole, anise oil, aromatic elixir, benzaldehyde, benzaldehyde elixir, cyclodextrins, caraway, caraway oil, cardamom oil, cardamom seed, cardamom spirit, cardamom tincture, cherry juice, cherry syrup, cinnamon, cinnamon oil, cinnamon water, citric acid, citric acid syrup, clove oil, cocoa, cocoa syrup, coriander oil, dextrose, eriodictyon, eriodictyon fluidextract, eriodictyon syrup, aromatic, ethylacetate, ethyl vanillin, fennel oil, ginger, ginger fluidextract, ginger oleoresin, dextrose, glucose, sugar, maltodextrin, glycerin, glycyrrhiza, glycyrrhiza elixir, glycyrrhiza extract, glycyrrhiza extract pure, glycyrrhiza fluid extract, glycyrrhiza syrup, honey, iso-alcoholic elixir, lavender oil, lemon oil, lemon tincture, mannitol, methyl salicylate, nutmeg oil, orange bitter, elixir, orange bitter, oil, orange flower oil, orange flower water, orange oil, orange peel, bitter, orange peel sweet, tincture, orange spirit, orange syrup, peppermint, peppermint oil, peppermint spirit, peppermint water, phenylethyl alcohol, raspberry juice, raspberry syrup, rosemary oil, rose oil, rose water, stronger, saccharin, saccharin calcium, saccharin sodium, sarsaparilla syrup, sarsaparilla, sorbitol solution, spearmint, spearmint oil, sucrose, sucralose, syrup, thyme oil, tolu balsam, tolu balsam syrup, vanilla, vanilla tincture, vanillin, wild cherry syrup, or combinations thereof.

Illustrative taste masking agents include, but are not limited to, cyclodextrins, cyclodextrins emulsions, cyclodextrins particles, cyclodextrins complexes, or combinations thereof.

Illustrative suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats.

Illustrative emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol.

The foregoing excipients can have multiple roles as is known in the art. For example, starch can serve as a filler as well as a disintegrant. The classification of excipients above is not to be construed as limiting in any manner.

Compositions of the present invention may be administered in any manner including, but not limited to, orally, parenterally, sublingually, transdermally, rectally, transmucosally, topically, via inhalation, via buccal administration, or combinations thereof. Parenteral administration includes, but is not limited to, intravenous, intraarterial, intraperitoneal, subcutaneous, intramuscular, intrathecal, intraarticular, intracisternal and intraventricular.

A therapeutically effective amount of the composition required for use in therapy varies with the length of time that activity is desired, and the age and the condition of the patient to be treated, among other factors, and is ultimately determined by the attendant physician. In general, however, doses employed for human treatment typically are in the range of about 0.001 mg/kg to about 500 mg/kg per day, for example about 1 µg/kg to about 1 mg/kg per day or about 1 µg/kg to about 100 µg/kg per day. For most large mammals, the total daily dosage is from about 1 to 100 mg, preferably from about 2 to 80 mg. The dosage regimen may be adjusted to provide the optimal therapeutic response. The desired dose may be conveniently administered in a single dose, or as multiple doses administered at appropriate intervals, for example as two, three, four or more subdoses per day.

Illustratively, a composition of the invention may be administered to a subject to provide the subject with an antiestrogen in an amount of about 1 µg/kg to about 1 mg/kg body weight, for example about 1 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg or about 1 mg/kg body weight.

In a preferred embodiment, compositions according to the present invention comprise trans-clomiphene at a dosage between one mg to about 200 mg (although the determination of optimal dosages is with the level of ordinary skill in the art).

The composition may comprise trans-clomiphene at a dosage of about 1 mg, 2 mg, 3, mg, 4 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg, 180 mg, 190 mg, 200 mg or there between. The composition may also comprise trans-clomiphene and cis-clomiphene at a ratio of about 71/29, 72/28, 73/27, 74/26, 75/25, 76/24, 77/23, 78/22, 79/21, 80/20, 81/19, 82/18, 83/17, 84/16, 85/15, 86/14, 87/13, 88/12, 89/11, 90/10, 91/9, 92/8, 93/7, 94/6, 95/5, 96/4, 97/3, 98/2, 99/1, 99.5/0.5 or there between. Analogs of the trans- and cis-isomers of clomiphene such as those described in Ernst, et al. supra are also useful in the practice of the present invention.

Compositions of the present invention may also be administered long-term. In this regard, the compositions may be administered for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more days. The compositions may also be administered for an administration period of at least 1, 2, 3, 4, 5, 6, 7, 8, 9, 10, 11, 12 or more months. The compositions may also be administered for an administration period of at least 1, 2, 3, 4, 5, 6, 7 8, 9, 10 or more years. During the administration period, the composition may be administered daily or periodically such as every other day and the like.

Compositions of the present invention may also be administered intermittently. For example, the compositions may be administered for an administration period of 1, 2, 3, 4, 5, or more weeks, followed by a period of discontinuance, followed by an administration period of 1, 2, 3, 4, 5 or more weeks, and so on.

All of the references referred to herein are incorporated by reference in their entirety.

The following Examples are meant to be illustrative of the invention and are not intended to limit the scope of the invention as set out is the appended claims.

EXAMPLE 1

Effects of Clomiphene and its Isomers on Serum Testosterone and Cholesterol in Male Baboons Adult, male, Baboons were given 1.5 mg/kg of Clomid (clomiphene citrate), Enclomid (trans-Clomiphene) or Zuclomid (cis-clomiphene) for 12 consecutive days. The samples analyzed were sera taken on the day of first treatment before being given test article (day 0), after 12 days of treatment (day 12) and 7 days after the last treatment (end or wash-out).

1. Effects on Body Weight and Serum LH, FSH, PRL and Testosterone

Figure 3:
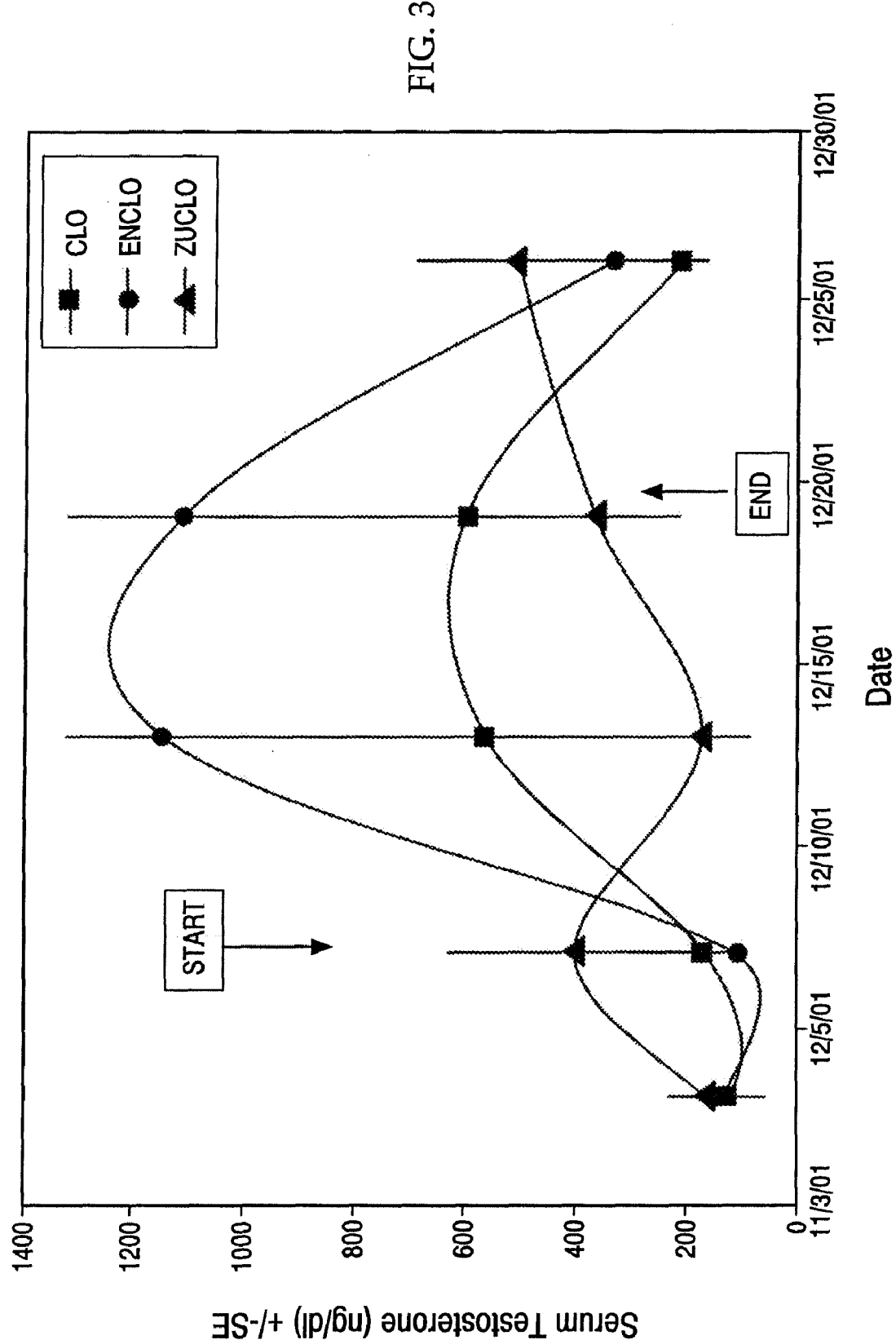
FIG. 3 is a graphic demonstration of the time course of serum testosterone levels with Clomid (clomiphene citrate), Enclomid (trans-clomiphene) and Zuclomid (cis-clomiphene).
Figure 4:
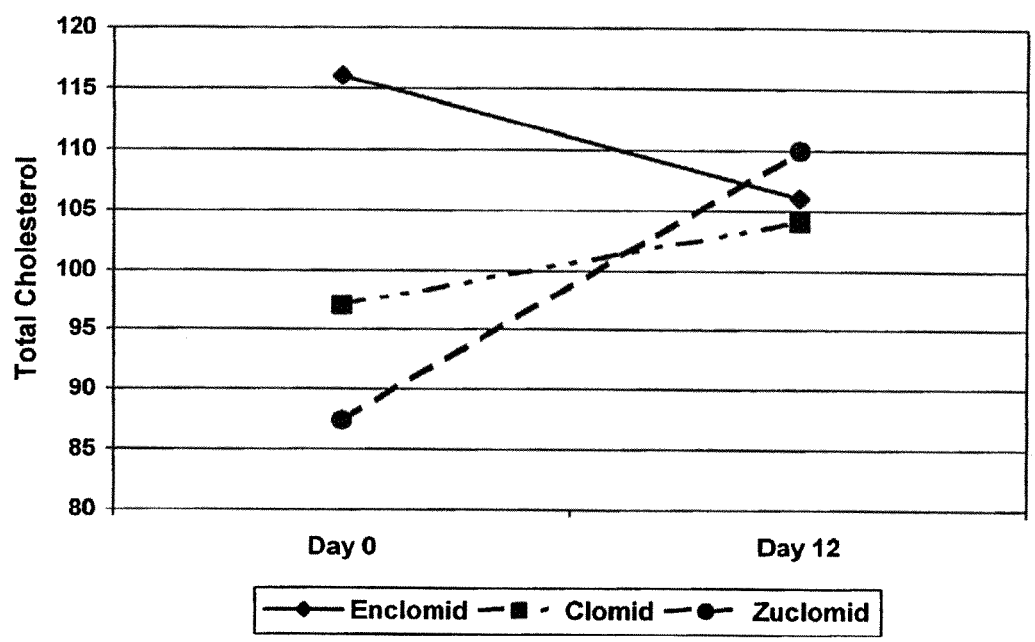
FIG. 4 is a graphic demonstration of the time course of cholesterol levels in baboon males treated with Clomid (clomiphene citrate), Enclomid (trans-clomiphene) and Zuclomid (cis-clomiphene).

There were significant increases in total serum testosterone in the group receiving Enclomid. See Table 1. There were no differences among groups in the baseline period or at day 0. There were also no differences among the three groups 7 days after treatment (the washout period). However, Enclomid produced higher levels of testosterone compared to Clomid and Zuclomid on day 6 ($p=0.03$ and $p=0.00002$ respectively) and compared to Zuclomid on day 12 ($p=0.047$). Zuclomid clearly did not raise total serum testosterone to any extent. Compared to the animals receiving Enclomid, the animals receiving Clomid exhibited more variable total testosterone levels on day 6 and later as judged by their coefficients of variations. When we looked at the time course of the effects (FIG. 3), we determined that only Enclomid significantly and statistically raised total serum testosterone on days 6 and 12 compared with either baseline or day 0 values. Moreover, cessation of Enclomid treatment, resulted in a significant drop in the level of total serum testosterone between day 12 and day 18 (washout). This indicates that Enclomid is readily cleared from the circulation consistent with the metabolic clearance seen for Enclomid in humans. Enclomid was clearly better and more consistent than Clomid itself and Zuclomid was ineffective.

gap, which were low for all nine baboons throughout the trial; (2) serum glucose; and (3) BUN which were high on day 0 for the group which would be treated with Enclomid. On day 12 of treatment and 7 days after treatment (washout), there were no differences among groups for any parameter except anionic gap that showed that the Clomid and Zuclomid groups had lower values than the Enclomid group. The values

TABLE 1

Serum Testosterone Levels (ng/dl)

| Group | ID | baseline Dec. 03, 2001 | 0 day Dec. 07, 2001 | 6 days Dec. 13, 2001 | 12 days Dec. 20, 2001 | wash-out Dec. 26, 2001 |
|---|---|---|---|---|---|---|
| CLO | 7500 | 79.01 | 76.15 | 940.97 | 891.5 | 150.9 |
|  | 9012 | 97.55 | 305.24 | 585.92 | 555.6 | 316.3 |
|  | 9097 | 158.06 | 102.94 | 151.12 | 318.9 | 143.6 |
|  | mean | 111.5 | 161.4 | 559.3 | 588.7 | 203.6 |
|  | SD | 41.3 | 125.2 | 395.6 | 287.7 | 97.7 |
| ENCLO | 7223 | 64.57 | 74.96 | 1223.8 | 633.6 | 307.2 |
|  | 8021 | 166.86 | 133.59 | 1128.2 | 1466 | 399.2 |
|  | 8369 | 170.45 | 106.47 | 1081.1 | 1166 | 271 |
|  | mean | 134.0 | 105.0 | 1144.4 | 1088.5 | 325.8 |
|  | SD | 60.1 | 29.3 | 72.7 | 421.6 | 66.1 |
| ZUCLO | 7438 | 124.84 | 210.4 | 137.51 | 314.5 | 359.7 |
|  | 8292 | 104.66 | 67.37 | 169.98 | 406.1 | 860.5 |
|  | 10098 | 282.29 | 904.82 | 227.95 | 353.0 | 274.1 |
|  | mean | 170.6 | 394.2 | 178.5 | 357.9 | 498.1 |
|  | SD | 97.3 | 448.0 | 45.8 | 46.0 | 316.8 |
|  | ANOVA | $p = 0.61$ | $p = 0.43$ | $p = 0.007$ | $p = 0.57$ | $p = 0.256$ |
|  | K-W | $p = 0.56$ | $p = 0.84$ | $p = 0.051$ | $p = 0.079$ | $p = 0.252$ |

There were no changes in serum LH or FSH. The ratio of total serum testosterone to LH followed the same pattern as total serum testosterone, suggesting a lack of dependence (data not shown). There was also no change in body weight during the 12 day study. There was a decrease in serum prolactin (PRL) during the study in the group receiving Enclomid, suggesting an effect of antiestrogen that has been described in part (Ben-Jonathan and Hnasko, 2001) and expected on the basis of the fact that as men age, testosterone declines and Prolactin increase (Feldman et al., 2002).

2. Effects on Cholesterol Levels

Treatment with Enclomid tended to decrease serum cholesterol and Zuclomid tended to increase the same parameter. Preliminary analysis indicated that the changes in cholesterol levels were not statistically significant and that the changes were within the normal range. Due to the observed trend for the two isomers to demonstrate opposite effects on cholesterol levels over a short period of time, further analysis was conducted.

Detailed analysis indicated that Enclomid resulted in an 8% decrease in serum cholesterol levels. Conversely, treatment with Zuclomid resulted in a 22% increase in serum cholesterol levels. Treatment with Clomid resulted in a slight increase in serum cholesterol levels. The opposite effect of Enclomid and Zuclomid on serum cholesterol levels is not unexpected given that the isomers have, alternatively, estrogen agonist or antagonist activity. These results indicate that Enclomid may be used for treating patients with high cholesterol levels. These results also indicate that Enclomid may be more benign than Zuclomid with respect to serum cholesterol if used chronically for increasing testosterone levels.

3. Effects on Clinical Chemistry Parameters

The mean values for each parameter did not differ among the three groups for any test parameter at the beginning of the study as determined by ANOVA or by the Kruskal-Wallis test. All groups exhibited normal values at each parameter except for (1) serum sodium; a related calculated parameter, anionic of serum sodium and anionic gap appear to be anomalies associated with this group of baboons.

There were substantive effects on the red blood cell population with Enclomid and Zuclomid and on hematocrit with Zuclomid. All the compounds lower the mean cell hemoglobin concentration (MCHC) either at day 0 or at the endpoint. With no change in mean cell hemoglobin (MCH) and an increase in the mean cell volume (MCV), the lowering of MCHC is predictable. Although testosterone might be expected to raise hematocrit, only Zuclomid treatment, which did not increase total serum testosterone, demonstrated a statistical difference. Clearly, men in a clinical trial that uses Zuclomid should be monitored for the characteristics of their red blood cell population. Enclomid would be predicted to have less of an effect.

There appears to be a clear effect of 12-day Enclomid treatment on platelets although the values found stayed within the normal range. One thing to consider here is the sexual dimorphism in platelet counts between male and female baboons (279 for males vs. 348 for females). This is likely to be due to hormones. Since the Enclomid group demonstrated increased testosterone, the lowering of the platelet count could be secondary to the change in testosterone in this group. Moreover, treatment with Enclomid pushed the platelet count to its normal male level from a day 0 level that was the high end of the normal range for this group. Enclomid would not necessarily predict a deleterious effect on platelets.

Clomiphene citrate, Enclomid and Zuclomid all had effects on the white blood cell (WBC) population, the most striking was that of Enclomid on raising the counts of lymphocytes and eosinophiles. The effects are not as straightforward as they would seem to be. There appears to be a strong effect of Enclomid on lowering the percent of granulocytes in the blood. The effects are very strong after the 7-day washout period when the values are decreased below the normal range. (This time course could reflect the relatively long time required to affect change the WBC population.) There is little sexual dimorphism in baboons with respect to the white blood cell populations, so the effects are more likely to be due to the compound itself than changes in testosterone. However, when we look at the calculated count of granulocytes using the WBC count, we find no differences in granulocyte count due to any compound. Concomitantly, it is the lymphocyte story that is the most interesting. Both the count and percent lymphocytes in the population increase with Enclomid treatment. Whereas the mean values of percent lymphocytes remain in the normal range, given the trend for an increase in WBC count, the net effect is an increase in lymphocyte count with Enclomid. This eosinophil result is analogous. There is a clear implication for treating men who have low lymphocytes, such as men who are HIV-positive. Since Enclomid is unlikely to lower lymphocytes based on this result, a case could be made for its use in the population of men with AIDS. These individuals are often treated with agents that are intended to raise testosterone due to the wasting effects of disease. Low liver and kidney toxicity and favorable effects on cholesterol and lipids are also highly favored attributes for any medication intended for use HIV-positive men who are already compromised by their disease.

The increase in serum glucose with Clomid or Zuclomid was within the normal range. In the case of Enclomid where the mean serum glucose values were high on day 0, there were no increases with treatment. There was no evidence that Enclomid would have a deleterious effect on blood glucose.

No clearly adverse effects on liver function are apparent as judged by the enzymes AST and ALT. The trend in these values was a decrease with treatment. An increase in the level of enzymes in the serum would indicate liver damage. ALT/SGPT was out of range low at the end of the study for the Clomid group although the differences over the treatment period were not statistically significant. The changes with Enclomid and Zuclomid were within the normal range. AST is depressed in pregnancy; thus the action of an estrogen agonist such as Zuclomid in lowering the marginal AST level could be rationalized. Alkaline phosphatase (ALP) is also found in the liver and is elevated various disease states. The lowering of ALP argues further against hepatic damage. There were no changes in serum albumin, also a liver product. A strong suppression of serum albumin over an extended time period could contribute to free serum steroid hormone levels in humans although a more important role is played by sex hormone binding globulin. As a bottom line, none of the compounds could be linked to liver damage on the basis of the parameters assayed.

Osteoblastic activity and diseases of the bone are accompanied by high serum ALP values. ALP was not elevated following Zuclomid treatment and was decreased in value following Enclomid treatment. The trends would predict a more benign result for the use of Enclomid compared to Zuclomid.

Although BUN and BUN/creatinine were altered during the study in the Clomid and Enclomid groups, the lack of a definitive change in creatinine argues against renal dysfunction. A loss of glomerular filtration capacity would result in an increase in BUN. Decreased BUN occurs in humans due to poor nutrition (not likely in a controlled setting), or high fluid intake (presumably accompanied by edema). Also, despite an increase in total serum testosterone between day 0 and Day 12 with Enclomid, there were no differences between serum creatinine values, arguing against an increase in muscle mass over this short time interval.

Serum sodium levels were lower than reference values for all animals throughout the study. Serum carbon dioxide was higher than reference values on day 12 for the Clomid and Zuclomid groups. Serum anion gap was lower for all animals throughout the study, paralleling the sodium results. Enclomid raised this parameter towards normal values. The electrolyte imbalances detected in the test animals throughout all treatment periods remains elusive but might be part of the same fluid derangement phenomenon suggested by the BUN results.

The foregoing results indicate that Enclomid is more effective than Clomid or Zuclomid at enhancing total serum testosterone. Zuclomid is clearly not effective and that deficiency limits any use of Clomid for hypogonadism, particularly since the Zuclomid component of Clomid would predominate in the circulation over time given its longer half-life.

Enclomid appeared to be relatively benign in all aspects when compared to Zuclomid and, often, even Clomid. This is particularly true when consideration is given to the trend of Enclomid to lower cholesterol, and liver enzymes as opposed to Zuclomid's trend to raise the same parameters. The surprising trend for Enclomid to raise the lymphocyte count may be useful for men with AIDS if it can be shown the CD4+ subpopulation of lymphocytes is not lowered or is enhanced.

EXAMPLE 2

Method for Treating Impaired Fasting Glucose in Men by Administration of Trans-Clomiphene And Mixtures of Trans-Clomiphene and Cis-Clomiphene at Ratios Greater than 71/29

Subject males undergo an overnight fast lasting from 8-12 hours after which blood samples are taken from subject males and fasting blood glucose levels are measured.

Subject males with fasting blood glucose levels between 110 and 125 mg/dl are given daily dosages of 1.5 mg/kg clomiphene, wherein the ratio of trans-clomiphene to cis-clomiphene is greater than 71/29. Fasting blood glucose levels are monitored at regular intervals such that the dosage amount and dosage frequency may be adjusted to achieve therapeutic fasting blood glucose levels in the subject.

EXAMPLE 3

Method for Treating Insulin Resistance in Men by Administration of Trans-Clomiphene and Mixtures of Trans-Clomiphene and Cis-Clomiphene at Ratios Greater than 71/29

Insulin sensitivity is assessed in subject males using, e.g., the hyperinsulinemic-euglycemic clamp as described in Defronzo et al., Am. J. Physiol. 237:E214-E223 (1979) and/or the homeostatic model assessment for insulin resistance (HOMA-IR) as described in Matthews et al., Diabetologia. 28:412-419 (1985).

Subject males with insulin resistance are given daily dosages of 1.5 mg/kg clomiphene, wherein the ratio of trans-clomiphene to cis-clomiphene is greater than 71/29. Insulin sensitivity is monitored at regular intervals such that the dosage amount and dosage frequency may be adjusted to achieve therapeutic increases in insulin sensitivity in the subject.

EXAMPLE 4

Comparison of Androxal™ to Androgel®

A placebo controlled challenge study was conducted at the Advanced Biological Research, Inc. (ABR) Clinical Research Center in Hackensack, N.J. to compare orally administered Androxal™ (trans-clomiphene) to Androgel® in hypogonadal men. Androgel® (Solvay Pharmaceuticals, Inc.) consists of a cream that administers exogenous testosterone in a transdermal matrix.

The study enrolled 62 hypogonadal men with testosterone levels less than 300 ng/dl (normal 298-1034 ng/dl) that were randomized into 6 different arms, three doses of Androxal™ (12.5 mg, 25 mg, and 50 mg), placebo, and both high and low doses of Androgel®. Half of the men in each of the Androxal™ and placebo arms were randomized into cohorts that underwent in-clinic sessions on days 1 and 14 to determine pharmacokinetic parameters for Androxal™ as well as cyclical changes in testosterone. The placebo and Androxal™ doses were administered in a double blind fashion. The Androgel® cream was administered in an open label fashion. Half of the Androgel® patients underwent in-clinic sessions similar to the other patients in the study. Following the two week drug exposure, patients were followed for an additional seven to ten days to determine the status of their testosterone levels. There were no side effects noted in either the Androxal™ or Androgel® arms of the study that were different than placebo.

1. Effects on Testosterone Levels

Figure 5:
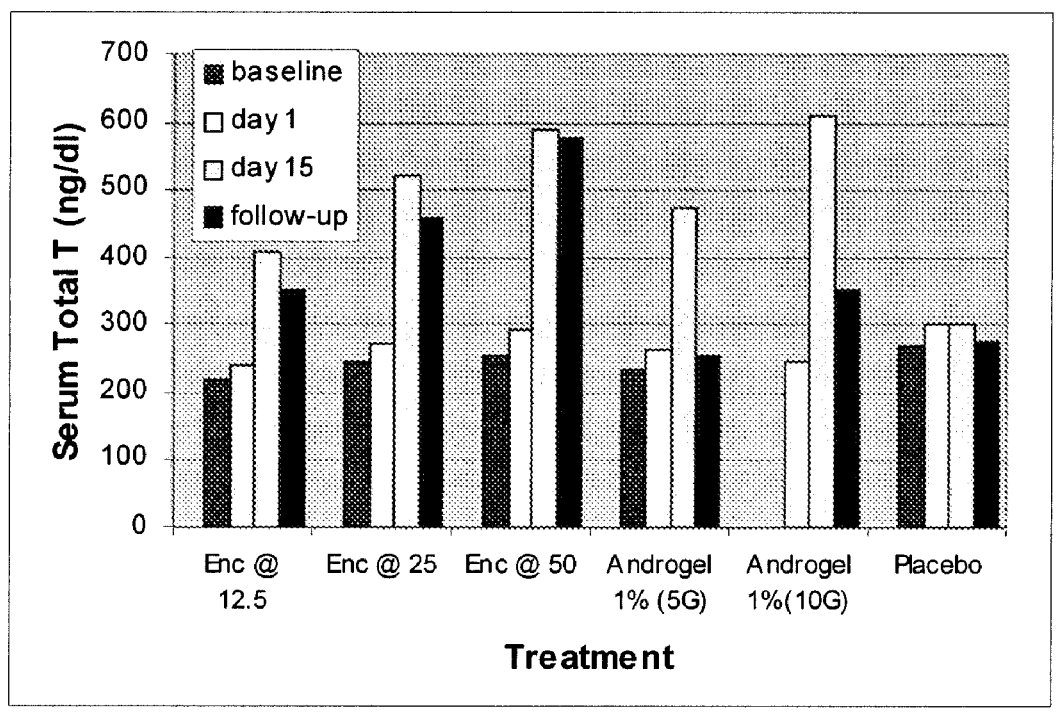
FIG. 5 demonstrates the effect of Androxal™ or Androgel® on testosterone levels.

All doses of Androxal™ or Androgel® produced statistically significant changes in testosterone from baseline testosterone levels (FIG. 5). The low, mid and high doses of Androxal™ achieved mean increases of 169, 247, and 294 ng/dl respectively, while those of Androgel® 5G, the lowest approved dose, and Androgel® 10G, the highest approved dose, produced changes from baseline that were 212 and 363 ng/dl. These values were statistically indistinguishable from those changes achieved with Androxal™. This inability to show differences between Androxal™ and Androgel® appears to result from the highly variable results found when Androgel® is used. For example the 50 mg dose of Androxal™ raised mean total testosterone to 589±172 ng/dl after 15 days, a coefficient of variation (CV) of 29% and similar to the placebo group (36%). On the other hand Androgel® 5G and 10G yielded mean total testosterone values 473±289 ng/dl and 608±323 ng/dl, CV's of 61% and 53% respectively.

After 14 days of Androxal™ therapy all doses were associated with a total testosterone diurnal pattern similar to the placebo group, i.e. a morning peak, a mid-day trough and a rise overnight. Without being bound by theory, this pattern may be due to the mode of action of Androxal™, which appears to be mediated through effects on the hypothalamic-pituitary axis as shown below. The diurnal pattern for men on Androgel® was nearly flat. However, spikes in total testosterone for Androgel® were associated with dosing and often exceeded the normal high level of 1,034 ng/dl. Certain individuals on Androgel® 10G were able to achieve peak levels of total testosterone of over 2500 ng/dl.

Interestingly, the level of serum total testosterone in the follow-up period (i.e., 7-10 days after cessation of daily oral treatment) unexpectedly remained high after treatment with Androxal™. In addition, the serum total testosterone levels were significantly higher at the highest dose of Androxal™ compared to the high dose of AndroGel® 1% (p=0.017, t-test).

2. Effects on LH and FSH Levels

Figure 6:
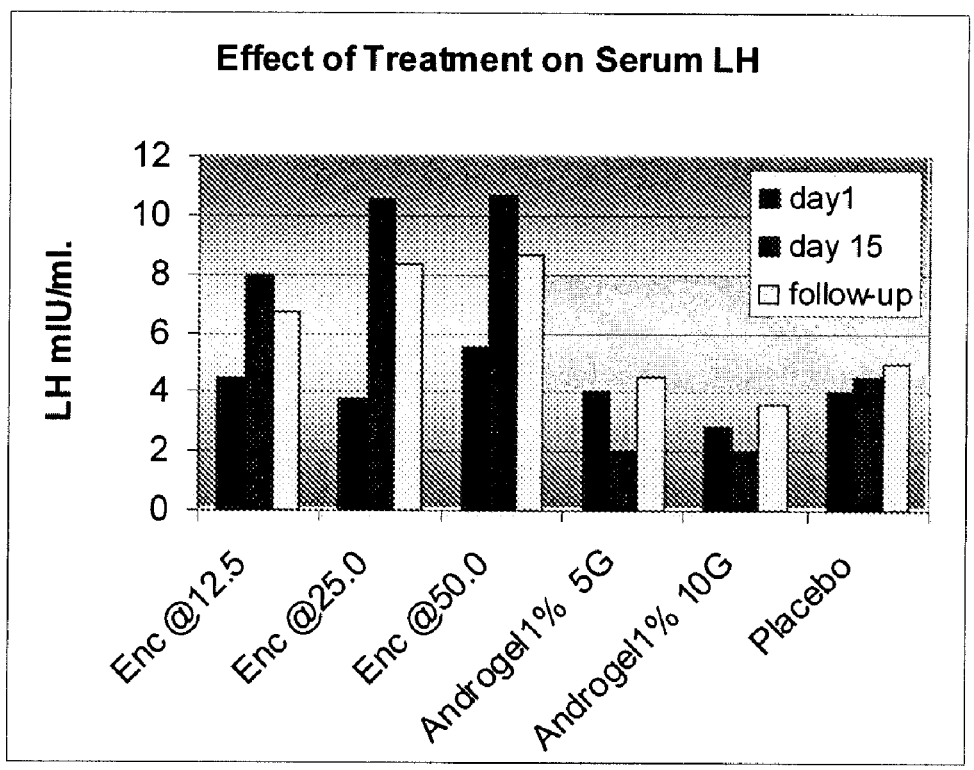
FIG. 6 demonstrates the effect of Androxal™ or Androgel® on LH levels.

Treatment with Androxal™ produced a statistically significant increase in the serum levels of LH in the hypogonadal male subjects (FIG. 6). As in the case of total serum testosterone there was an unexpected continuation in the level of serum LH in the follow-up period (i.e., 7-10 days after cessation of daily oral treatment) where those levels remained high for the three doses of Androxal™. By comparison, treatment with AndroGel® initially decreased LH and after cessation there was an apparent rebound towards pre-treatment levels.

Figure 7:
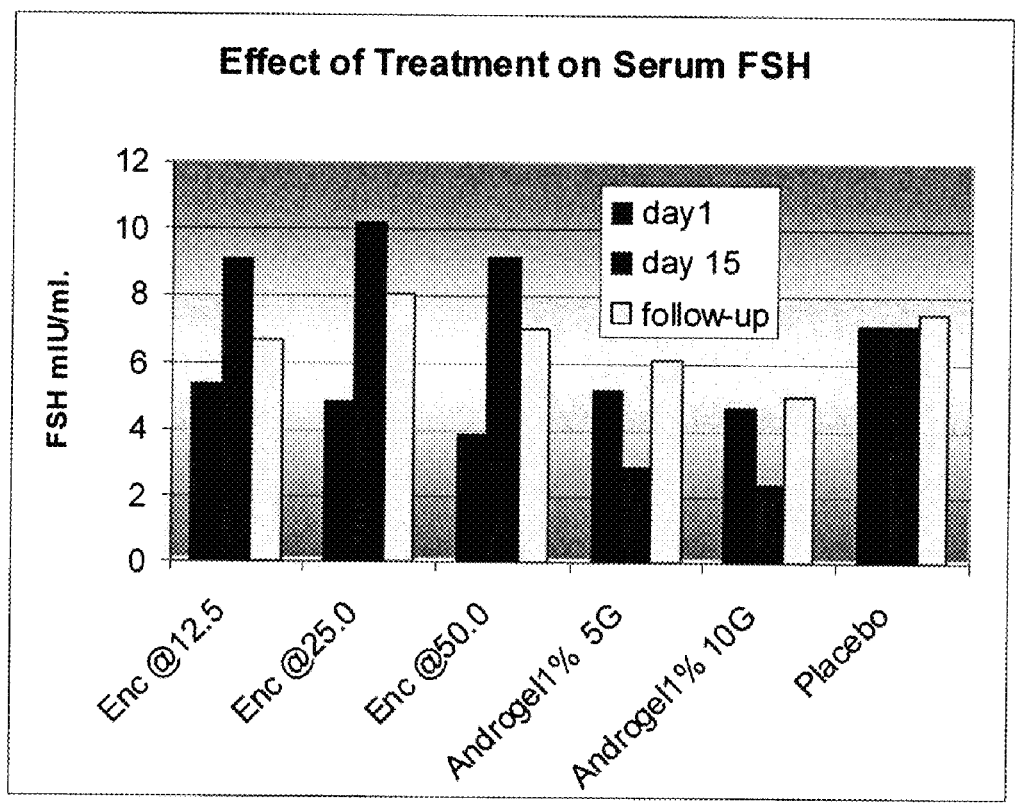
FIG. 7 demonstrates the effect of Androxal™ or Androgel® on FSH levels

Treatment with Androxal™ also produced a statistically increase in the serum levels of FSH in the hypogonadal male subjects (FIG. 7). The pattern of increasing FSH is similar to that seen in the case of LH, that is, all doses of Androxal™ boosts serum FSH which remains high during the follow-up period whereas AndroGel® suppresses the level of serum FSH and cessation of treatment allows serum FSH to rebound towards concentrations more similar to pre-treatment levels.

3. Effects on Other Clinical Chemistry Parameters

The effect on serum dihydroxytestosterone (DHT) levels were also measured. Men on Androxal™ experienced a favorable shift in their DHT to total testosterone. For example men on the 50 mg dose of Androxal™ experienced a DHT/TT ratio of 0.83 as compared to the placebo group ratio of 1.07. By contrast the DHT/TT ratio for either of the Androgel® groups was >1.5. The results indicate that men on Androgel® were gaining DHT faster than total testosterone. Thus the normal levels of DHT was disrupted relative to testosterone in men on Androgel® therapy.

Results of clinical chemistry parameters also indicated, unexpectedly, that men on Androxal™ experienced a non-dose dependent reduction in triglycerides. The reduction in triglycerides averaged a decrease of 19.1% after two weeks of therapy. This compared to a 5.9% reduction for the placebo group and increases of 0.3% and 22% for the Androgel® 50 and 10G respectively.

4. Discussion

Based on this study we infer a number of potential advantages for Androxal™ as a potential therapy. Androxal™ appears to raise total testosterone into the normal range in a highly consistent manner without abnormally high spikes in serum testosterone. In addition, the use of trans-clomiphene to treat men that suffer secondary hypogonadism offers a new approach that potentially could offset one of the major side effects of exogenous therapies such as Androgel®. Exogenous therapies provide negative feedback thereby shutting down FSH and LH production. FSH is an essential reproductive hormone and in the male stimulates spermatogenesis. Long term exposure to exogenous testosterone, as a result of its effects on FSH production, causes a reduction in sperm synthesis, leading to the potential for transient infertility due to low sperm counts and therefore a resulting shrinkage of the testis, since the volume of the testis is related to the level of spermatogenesis within the seminiferus tubules. The increase in FSH levels also indicates that Androxal™ may be used to treat infertility in males, including hypogonadal males. Moreover, the extended affects of Androxal™ on serum testosterone, FSH and LH levels indicate that Androxal™ may be administered with altered dosages or scheduling, allowing perhaps even non-daily or episodic treatment.

EXAMPLE 5

Effect of Trans-Clomiphene on Fasting Glucose Levels

A placebo controlled study was conducted to determine the effects of orally administered Androxal™ (trans-clomiphene) and Androgel® on blood glucose levels.

Androgel® (Solvay Pharmaceuticals, Inc.) consists of a cream that administers exogenous testosterone in a transdermal matrix.

Figure 8:
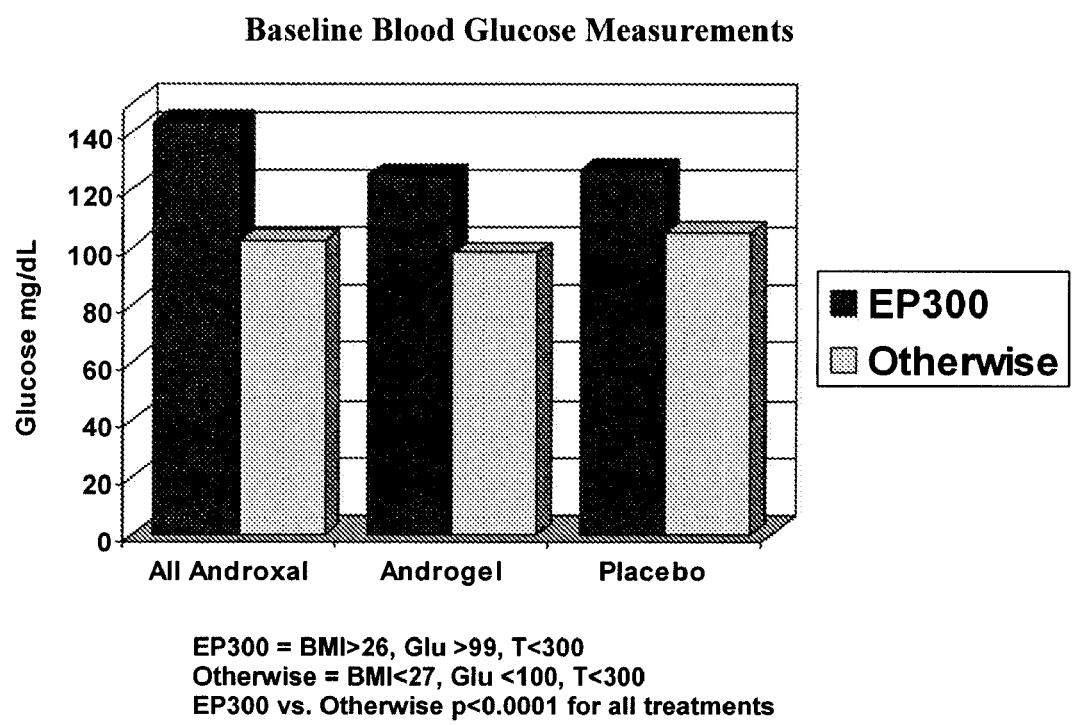
FIG. 8 demonstrates baseline blood glucose in Androxal™, Androgel® and placebo treatment groups.

The study enrolled hypogonadal men (testosterone less than 300 ng/dl) with a broad range of body mass indices (BMI). Patients were randomized into 3 different arms, 50 mg dose of Androxal™, placebo, and high dose of Androgel®. The placebo and Androxal™ doses were administered in a double blind fashion. The Androgel® cream was administered in an open label fashion. Fasting glucose levels were monitored in the patients immediately prior to treatment (baseline) and at regular intervals during the study. There were no side effects noted in either the Androxal™ or Androgel® arms of the study that were different than placebo FIG. 8 depicts the baseline blood glucose levels of each treatment group. The patients in each treatment group are separated on the graph according to BMI. Dark shaded bars depict baseline blood glucose in patients in each treatment group with BMI>26 (EP300). Light shaded bars depict baseline blood glucose in patients in each treatment group with BMI<27. As can be seen from FIG. 8, baseline blood glucose in patients with BMI>26 was significantly elevated in all treatment groups relative to patients with BMI<27.

Figure 9:
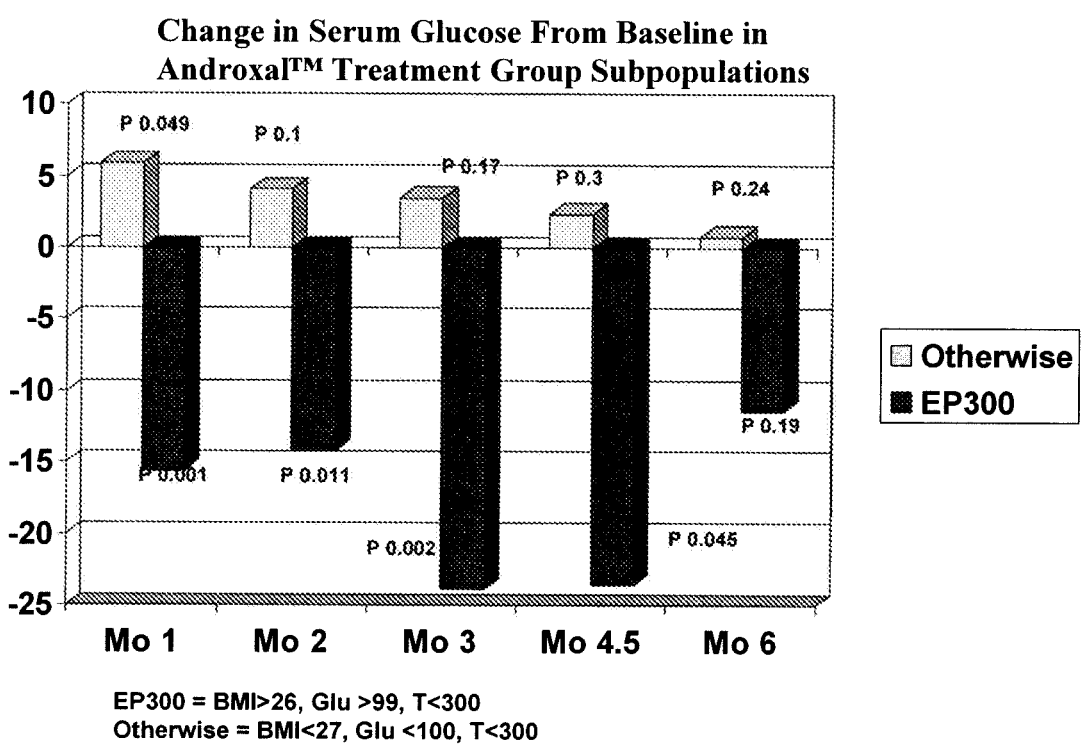
FIG. 9 demonstrates the effect of Androxal™ on blood glucose levels.

FIG. 9 depicts changes in serum glucose from baseline in the Androxal treatment group. The patients are separated on the graph according to BMI. Dark shaded bars depict changes in serum glucose from baseline in patients with BMI>26 (EP300). Light shaded bars depict changes in serum glucose from baseline in patients with BMI<27. As can be seen from FIG. 9, treatment with Androxal was effective in lowering serum glucose levels in patients with BMI>26 throughout the treatment period, with a reduction of nearly 24 mg/dl observed at the 3 and 4.5 month periods.

Figure 10:
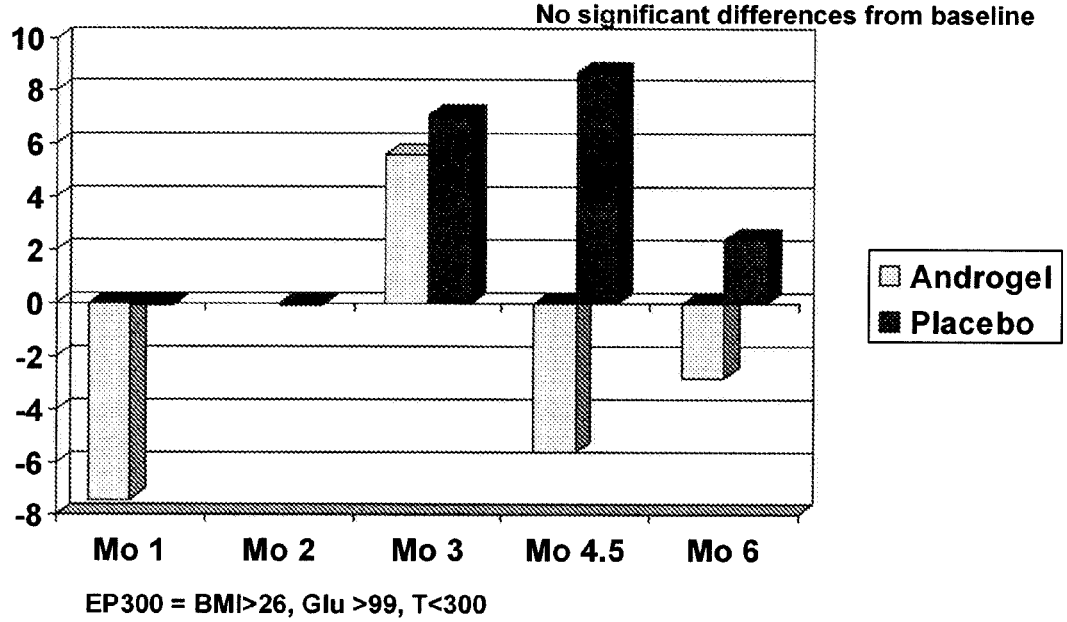
FIG. 10 demonstrates the effect of Androgel® on blood glucose levels.

FIG. 10 depicts changes in serum glucose from baseline in the Androgel® and Placebo treatment groups in patients with BMI>26 (EP300). Dark shaded bars depict changes in serum glucose from baseline in patients in the placebo group. Light shaded bars depict changes in serum glucose from baseline in patients in the Androgel® treatment group. As can be seen from FIG. 10, no significant differences in serum glucose from baseline were observed in patients with BMI>26 in either Androgel® or placebo treatment groups.

These data suggest that Androxal™ is surprisingly effective in reducing fasting glucose levels (and accompanying insulin resistance) in patients with low normal or below normal testosterone who have developed metabolic syndrome and demonstrates efficacy of Androxal™ in treating metabolic syndrome and conditions associated therewith such as elevated glucose levels, elevated triglyceride levels, elevated, elevated cholesterol levels, insulin resistance, high blood pressure and obesity. In contrast, administration of exogenous testosterone is ineffective in reducing glucose levels in patients with low normal or below normal testosterone who have developed metabolic syndrome.

The invention claimed is:

1. A method for treating type 2 diabetes in human male with secondary hypogonadism and having a body mass index greater than 26 comprising administering to said subject with secondary hypogonadism in need of treatment for type 2 diabetes an effective amount of a composition comprising about 100% w/w of active ingredients of trans-clomiphene or a salt thereof to treat type 2 diabetes in the subject.

2. The method of claim 1, wherein the subject has a fasting glucose level between 125 and 140 mg/dl prior to said administration.

3. The method of claim 1, wherein said administration reduces fasting glucose levels below about 110 mg/dl in said subject.

4. The method of claim 1, wherein the dosage of trans-clomiphene is from about 12.5 to about 50 mg.

5. The method of claim 4, wherein the dosage of trans-clomiphene is 12.5 , 25 or 50 mg.

6. The method of claim 1, wherein the testosterone level of said subject is below 300 ng/dl.

7. The method of claim 1, wherein said subject has a fasting blood glucose level between 110 mg/dl and 125 mg/dl.

8. The method of claim 1, wherein said administration reduces the fasting blood glucose level in said subject below 110 mg/dl.

* * * * *